US005645845A

United States Patent [19]

Neumann et al.

[11] Patent Number: 5,645,845

[45] Date of Patent: Jul. 8, 1997

[54] INSECTICIDE-COMPRISING GEL FORMULATIONS FOR VAPOR-PRODUCING SYSTEMS

[75] Inventors: Hermann Neumann, Haan; Dietmar Kalder, Leverkusen, both of Germany

[73] Assignee: Bayer Aktiengesellschaft, Leverkusen, Germany

[21] Appl. No.: 501,748

[22] Filed: Jul. 12, 1995

[30] Foreign Application Priority Data

Jul. 14, 1994 [DE] Germany .......................... 44 24 786.9

[51] Int. Cl.[6] ........................ A01N 25/04

[52] U.S. Cl. ........................ 424/405; 424/409; 424/421

[58] Field of Search ........................ 424/405, 409, 424/421

[56] References Cited

U.S. PATENT DOCUMENTS

| | | | |
|---|---|---|---|
| 3,337,399 | 8/1967 | Dawson | 167/39 |
| 4,037,353 | 7/1977 | Hennart et al. | 43/129 |

FOREIGN PATENT DOCUMENTS

| | | |
|---|---|---|
| 0579245 | 1/1994 | European Pat. Off. . |
| 2002635 | 2/1979 | United Kingdom . |
| 2022417 | 12/1979 | United Kingdom . |

OTHER PUBLICATIONS

Derwent Database, Week 8404, AN 83–08679K, abstract of JP 57–203,002, (1982).

Derwent Database, Week 9039, AN 90–294260, abstract of JP 02–207,002, (1990).

Derwent Database, Week 8747, AN 87–330752, abstract of JP 62–235562, (1987).

*Primary Examiner*—Neil S. Levy

*Attorney, Agent, or Firm*—Sprung Horn Kramer & Woods

[57] ABSTRACT

The present invention relates to new gel formulations for the controlled and sustained release of insecticidal active compounds by means of a heat source, these gel formulations comprising at least one pyrethroid-type insecticidal active compound and at least one vaporization-controlling substance in combination with an inorganic solid suitable as a gel former.

11 Claims, No Drawings

INSECTICIDE-COMPRISING GEL FORMULATIONS FOR VAPOR-PRODUCING SYSTEMS

The present invention relates to new gel formulations for the controlled and sustained release of insecticidal active compounds by means of a heat source. These new gel formulations are characterized in that they comprise at least one type of insecticide, and at least one vaporization-controlling substance (vaporization modifier) in combination with a solid suitable as a gel former.

The object of the present invention consists in formulating insecticidal active compounds in such a manner that the latter are not only storage-stable, but are additionally suitable, in conjunction with organic and inorganic adjuvants, stabilizers, antioxidants, perfumes and colorants, for uniform and prolonged vaporization by means of a heat source without undergoing decomposition. This is intended to achieve an optimum effectiveness and duration of action while keeping the energy input as low as possible. This new active compound formulation is intended to be employed in thermoformed, deep-dram or cast containers, made of polymer or metal, which are open or closed by a suitable fabric, polymer films, for example polypropylene film, or metal, these being permeable to the volatile components. These thermoformed or deep-drawn containers can be employed in an electrical heating device for killing insects, for example mosquitoes. Examples of such thermoformed or deep-drawn containers are described in U.S. Pat. No. 4,634,614, WO 81/0241, U.S. Pat. No. 4,145,001 and European Offenlegungsschrift 0,300,286.

In the case where mosquitoes are killed using an electrical heating device, a so-called tablet vaporizer, it is generally known that specifically selected substances, such as cellulose board and cotton board, asbestos, ceramics and/or porous synthetic resins are impregnated with pyrethroid insecticides to obtain insecticide tablets, the insecticides being volatilized by the action of the mosquito killer heating device, which generates a temperature of 120°–190° C.

A considerable disadvantage of these tablet vaporizers is the unfavorable ratio between energy input and active compound to be vaporized, since the proportion of active compounds relative to the adjuvants are to be considered as low. Furthermore, the high working temperature of these tablet vaporizers means that only few active compounds are suitable for this purpose in the first place, and that, moreover, these active compounds are released over their predetermined period of action in a non-uniform manner, for system reasons. The period of action of these vaporizer tablets is limited to a maximum of 12 hours. Finally, the unfavorable ratio of active compound/carrier requires a substantial, constantly available stock of vaporizer tablets, which means that large amounts of material are necessary as carriers and packaging material.

The devices which are already widely used for domestic premises, in which a solution of an insecticidal active compound is vaporized by means of a heated wick (GB2153227) and where the active compound is dissolved in a kerosene mixture of saturated aliphatic hydrocarbons which is vaporized electrically by means of the wick, also have considerable disadvantages.

Apart from the fact that these vapor-producing systems also operate at temperatures of between 120° and 190° C., they require a specific distribution system (wick) and considerable amounts of solvents. When the product is used, the superproportional amount of solvents relative to the active compound results in a high concentration of solvents or adjuvants in the room, which, in turn, leads to dirtying of walls and objects in the vicinity of these devices, which has frequently been observed by consumers and given cause for complaint.

Other disadvantages of these formulations are the high volume of the solvent containers and the risk of the solvent leaking, which means that there are substantial problems during transport and hazards in use.

The present invention therefore relates to a gel formulation of insecticides which avoids all the above-described disadvantages, which is, moreover, simple to use, that is to say for example in vapor-producing devices which are known already, of the type described in EP 0 321 729, and which at the same time guarantees uniform release of the active compound over up to 100 days, preferably up to 60 days, while operating at a low temperature of 70°–120° C.

The insecticide-comprising gel formulations according to the invention include mixtures which comprise at least one type of a pyrethroid insecticide, one vaporization-controlling substance and one inorganic solid which is suitable as gel former. Moreover, organic or inorganic adjuvants, stabilizers, perfumes and colorants may be added to the mixtures.

The gel formulations according to the invention are prepared by first stirring at room temperature in a suitable mixing apparatus (planetary paddle mixer) the active compound with the vaporization modifier and stabilizer and, if appropriate, additional solvents, until a clear solution is formed. Then, the gel former is added in vacuo, and the mixture is stirred vigorously until a homogeneous gel is formed. Before the gel former is mixed in to give the final gel product, perfume oils and colorants can optionally be added to the existing clear solution with stirring until the mixture is completely homogeneous.

The following are preferably used as pyrethroid active compounds:

1) Natural pyrethrum;
2) 3-allyl-2-methylcyclopenta-2-en-4-on-1-yl DL-cis/trans-chrysanthemate (allethrin, Pynamin®);
3) 3-allyl-2-methylcyclopenta-2-en-4-on-1-yl D-cis/trans-chrysanthemate (Pynamin forte®);
4) D-3 -allyl-2-methylcyclopenta-2-en-4-on-1-yl D-trans-chrysanthemate (Exrin®);
5) 3 -allyl-2-methylcyclopenta-2-en-4-on- 1-yl D-trans-chrysanthemate (Bioallethrin®);
6) N-(3,4,5,6-tetrahydrophthalimide)-methyl DL-cis/trans-chrysanthemate, (phtalthrin, Neo-pynamin®);
7) 5-benzyl-3-furylmethyl D-cis/trans-chrysanthemate (resmethrin, Chrysron-forte®);
8) 5-(2-propargyl)-3-furylmethyl chrysanthemate (furamethrin);
9) 3-phenoxybenzyl 2,2-dimethyl-3-(2',2'-dichlorovinyl)-cyclopropane-carboxylate (permethrin, Exmin®);
10) phenoxybenzyl D-cis/trans-chrysanthemate (phenothrin, Sumithrin®);
11) α-cyano-3-phenoxybenzyl 2-(4-chlorophenyl)-3-methylbutyrate (fenvalerate, Sumicidin®);
12) (S)-α-cyano-3-phenoxybenzyl (1R, cis)-3-(2,2-dichlorovinyl)-2,2-dimethylcyclopropane carboxylate;
13) (R,S)-α-cyano-3-phenoxybenzyl (1R, 1S)-cis/trans-3-(2,2-dichlorovinyl)-2,2-dimethylcyclopropane carboxylate;
14) α-cyano-3-phenoxybenzyl D-cis/trans-chrysanthemate;
15) 1-ethinyl-2-methyl-2-pentenyl cis/trans-chrysanthemate;
16) 1-ethinyl-2-methyl-2-pentenyl 2,2-dimethyl-3 -(2-methyl-1-propenyl)cyclopropane-1-carboxylate;
17) 1-ethinyl-2-methyl-2-pentenyl 2,2,3,3 -tetramethylcyclopropane-carboxylate;
18) 1-ethinyl-2-methyl-2-pentenyl 2,2-dimethyl-3-(2,2-dichlorovinyl) cyclopropane-1-carboxylate;
19) 2,3,5,6-tetrafluorobenzyl (+)-1R-trans-2,2-dimethyl-3-(2,2-dichlorovinyl)cyclopropane-carboxylate (transfluthrin)

20) (RS)-2-methyl-4-oxo-3-prop-2-ynylcylopent-2-enyl (1RS)-cis/trans-2,2-dimethyl-3-(2-methylprop-1-enyl) cyclopanecarboxylate or mixtures of these active compounds.

The active compound 2,3,5,6-tetrafluorobenzyl (+)-1R-trans-2,2-dimethyl-3-(2,2-dichlorovinyl)cyclopropanecarboxylate (transfluthrin) is particularly preferably used.

Vaporization-controlling substances, so-called vaporization modifiers, which can be employed are (poly)aromatic as well as acyclic hydrocarbons in pure form and in the form of mixtures. The following are preferably employed: diphenyl, diphenyl ether, o-, m-, p-terphenyl, mixtures of hydrogenated hydrocarbons, for example in their commercially available forms, Diphyl THT® an isomeric mixture of partially hydrogenated terphenyls available from Bayer Aktiengesellschaft, Santotherm®, Therm S 900®, butyl stearate, butyl oleate, methylacetyl ricinoleate, diethylglycol distearate; Isopar V®, Exol D140®, butoxyethyl stearate, tetrahydrofurfuryl oleate, epoxymethyl stearate, epoxybutyl oleate and the like; dibasic aliphatic acid esters, for example didecyl adipate, di-2-ethylene adipate, dimethoxyethyl adipate, di-2-ethylene azelate, diisodecyl azelate, di-2-ethylhexyl sebacate, dibutyl sebacate, dioctyl malate, dioctyl fumarate and the like; aromatic carboxylic esters, for example diethyl glycol benzoate, trioctyl trimellitate, tri(2-ethylhexyl) trimesate and the like; inorganic acid esters, for example tricresyl phosphate, tri-2-ethylhexyl phosphate, tributyl phosphate and the like; phthalic esters, for example di-2-ethylhexyl phthalate, dibutyl phthalate, diisobutyl phthalate, dicyclohexyl phthalate and the like, citric esters, for example triethyl citrate, tributyl citrate, tributylacetyl citrate and the like.

Particularly preferred vaporization modifiers are:

Butyl stearate, butyl oleate, methylacetyl ricinoleate, diethylene glycol, di-2-ethyl-hexyl sebacate, dioctyl fumarate, diethylene glycol benzoate, tri-2-ethylhexyl trimellitate, tricresyl phosphate, tri-2-ethylhexyl phosphate, di-2-ethylhexyl phthalate, o-, m-, p-terphenyl, didecyl phthalate, tributylacetyl citrate, tributyl citrate, diphyl THT®, Santotherm® or Therm S900®.

Very particularly preferred vaporization modifiers are Diphyl THT®, Santotherm® Thetin S900® or o-, m-, p-terphenyl.

Diphyl THT® is especially preferably employed as vaporization modifier.

Gel formers which are employed are highly-disperse silicas such as, for example, Aerosilox 50®, Aerosil 50®, Aerosil 130®, Aerosil 150®, Aerosil 200®, Aerosil 300®, Aerosil 380®, Aerosil Mox80®or sodium stearate.

Preferred gel formers which are employed are Aerosil 200®, Aerosilox 50®, Aerosil 50®, Aerosil 130®, Aerosil 150®, Aerosil 300®, Aerosil 380®or Aerosil Mox80®.

Aerosil 200® is especially preferably used as gel former.

The insecticide-comprising gel formulations according to the invention can be stabilized with the aid of antioxidants by admixing, to the formulation, a UV absorber as an additive. UV absorbers which can be employed are all known UV absorbers.

UV absorbers which are preferably employed are phenol derivatives such as, for example, butylhydroxytoluene (BHT), butylhydroxyanisole (BHA), bisphenol derivatives, arylamines such as, for example, phenyl-α-naphthylamine, phenyl-β-naphthylamine, a condensate of phenetidine and acetone or the like, or benzophenones.

The following are suitable organic and inorganic adjuvants:

Ammonium salts and ground natural rocks such as kaolins, clays, talc, chalk, quartz, attapulgite, montmorillonite or diatomaceous earth, and ground synthetic minerals, such as highly-disperse silica, alumina and silicates; as solid carriers for granules there are suitable:

for example crushed and fractionated natural rocks such as calcite, marble, pumice, sepiolite, dolomite, and synthetic granules of inorganic and organic meals, as well as granules of organic material, such as sawdust, coconut shells, maize cobs and tobacco stalks; as emulsifying and/or foam-forming agents there are suitable:

for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and albumen hydrolysates; as dispersants there are suitable:

for example lignin-sulfite waste liqors and methylcellulose.

Adhesives such as carboxymethylcellulose and natural and synthetic polymers in the form of powders, granules or latexes, such as gum arabic, polyvinyl alcohol, polyvinyl acetate, as well as natural phospholipids, kephalins and lecithins, and synthetic phospholipids can be used in the insecticide-comprising gel formulations according to the invention. Other additives can be mineral and vegetable oils.

It is possible to use colorants such as inorganic pigments, such as iron oxide, titanium oxide and Prussian Blue, and organic dyestuffs, such as alizaryn dyestuffs, azo dyestuffs and metal phthalocyanine dyestuffs, and trace nutrients such as salts of iron, manganese, boron, copper, cobalt, molybdenum and zinc.

These colorants which are added to the gel formulations according to the invention allow, on the one hand, the gel in the film container to be clearly seen, and, on the other hand, can be used for visually detecting the end of the biological activity of the system.

To this end, the film container together with the colored gel is introduced into a heating device whose front is transparent or provided with an observation slit.

As the heating device is used, the contents of the film container, not visible by color labeling on the container itself or on the heating device, dry.

Only the empty film container can be seen through the transparent front of the heating device or through the observation slit.

A further variant of visually can be also effected by changing detecting the end by adding colorants the color to a different color when the active substances and, if appropriate, the solvent have evaporated.

Deodorants may be added to the formulations according to the invention, such as, for example, lauryl methacrylate, geranyl crootonate, acetophenone myristate, p-methylacetophenone benzaldehyde, benzyl acetate, benzyl propionate, amyl cinnamaldehyde, anisaldehyde, diphenyl oxide, methyl benzoate, ethyl benzoate, methylphenyl acetate, ethylphenyl acetate, neoline, safrole, and the like.

Other substances which can furthermore be added to the formulations according to the invention are natural perfumes such as, for example, musk, cibet, ambergris, castoreum and similar perfumes; ajowan oil, almond oil, absolute of amberseed, angeliac root oil, aniseed oil, basil oil, bay oil, benzoin resinold, essence of bergamot, birch oil, rosewood oil, absolute of common broom, cajeput oil, cananga oil, capsicum oil, caraway oil, cardamon oil, carrot seed oil, cassia oil, cedar wood oil, celery seed oil, cinnamon bark oil, citronella oil, clary sage oil, clove oil, cognac oil, coriander oil, cubeb oil, camphor oil, dill oil, taragon oil, eucalyptus oil, sweet fennel oil, galbanum resinoid, garlic oil, geranium oil, ginger oil, grapefruit oil, hop oil, absolute of hyacinth, absolute of jasmin, juniper berry oil, labdanum resinoid, lavender oil, bay leaf oil, lemon oil, lemon grass oil, lovage oil, mace oil, mandarin oil, absolute of mimosa, absolute of myrrh, mustard oil, absolute of narcissus, neroli oil, bitter orange, nutmeg oil, absolute of oak moss, olibanum resinoid, onion oil, opoponax resinoid, orange oil, orange flower oil, concrete iris, pepper oil, peppermint oil, Perubalsam, petitgrain oil, pine needle oil, absolute of rose, rose oil, rosemary oil, sandalwood oil, sage oil, spearmint oil, storax oil, thyme oil, balsa of tolu, absolute of tonka bean, absolute of tuberose, terpentine oil, absolute of vanilla pod, vetiver oil, absolute of violet leaves, ylang-ylang oil and similar vegetable oils and the like.

Synthetic perfumes which can be added to the gel formulations according to the invention are:

pinene, limonene and similar hydrocarbons; 3,3,5-trimethylcyclohexanol, linalool, geraniol, nerol, citronellol, menthol, bomeol, borneylmethoxycyclohexanol, benzyl alcohol, anisyl alcohol, cinnamyl alcohol, β-phenylethyl alcohol, cis-3-hexanol, terpineol and similar alcohols; anethole, musk xylene, isoeugenol, methyleugenol and similar phenols; α-amylcinnamaldehyde, anisaldehyde, n-butyraldehyde, cuminaldehyde, cyclamenaldehyde, decyl aldehyde, isobutyraldehyde, hexyl aldehyde, heptyl aidehyde, n-nonyl aldehyde nonadienol, citral, citronellal, hydroxycitronellal, benzaldehyde, methylnonyl acetaldehyde, cinnamaldehyde, dodecanol, α-hexylcinnamaldehyde, undecanal, heliotropin, vanillin, ethylvanillin, and similar aldehydes, methyl amyl ketone, methyl 13-naphthyl ketone, methyl nonyl ketone, musk ketone, diacetyl, acetylpropionyl, acetylbutyryl, carvone, methone, camphor, acetophenone, p-methylacetophenone, ionone, methylionone and similar ketones; amylbutyrolactone, diphenyl oxide, methylphenyl glycidate, nonylacetone, coumarin, cineol, ethylmethylphenyl glycidate and similar lactones or oxides, methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl caproate, butyl heptylate, octyl caprylate, methyl heptinecarboxylate, methyl octinecarboxylate, isoamyl caprylate, methyl laurate, ethyl myristate, methyl myristate, ethyl benzoate, benzyl benzoate, methylcarbinylphenyl acetate, isobutylphenyl acetate, methyl cinnamate, styracin, methyl salicylate, ethyl anisate, methyl anthranilate, ethyl pyruvate, ethyl α-butylbutyrate, benzyl propionate, butyl acetate, butyl butyrate,-p-tert-butylcyclohexyl acetate, cedryl acetate, citronellyl acetate, citronellyl formate, p-cresyl acetate, ethyl butyrate, ethyl caproate, ethyl cinnamate, ethylphenyl acetate, ethylene brassylate, geranyl acetate, geranyl formate, isoamyl salicylate, isoamyl isovalerate, isobornyl acetate, linalyl acetate, methyl anthranilate, methyl dihydrojasmonate, nonyl acetate, β-phenylethyl acetate, trichloromethylenephenylcarbinyl acetate, terpinyl acetate, vetiveryl acetate and similar esters. These perfumes can be used on their own, or it is possible to use at least two thereof as a mixture with each other. In addition to perfume, the formulation according to the invention can, if appropriate, additionally comprise the additives conventionally used in the perfume industry, such as patchouli oil or similar volatilization inhibitors, such as eugenol, or similar viscosity regulators.

In addition to the insecticidal active compounds, the gel formulations according to the invention can include battericides and fungicides used in technology, such as, for example, 2,4,4-trichloro-2'-hydroxyphenyl ether, 2,3,5,6-tetrachloro-4-(methylsulfonyl)-pyridine, alkylbenzyldimethylammonium chloride, benzyldimethyl-(2-)2-(p-1,1,3,3-tetramethylbutylphenoxy)ethoxy)ethyl)ammonium chloride, 4-isopropyltropolone, N-dimethyl-N-phenyl-N'-(fluorodichloromethylthio)sulfonamide, 2-(4'-thiazolyl)-benzimidazole, N-(fluorodichloromethylthio)phthalimide, 6-acetoxy-2,4-dimethyl-m-dioxin, and the like, and bactericides and fungicides used in agriculture, such as, for example, zinc ethylenebisdithiocarbamate, manganese ethylenebisthiocarbamate, zinc maneb complex, bisdimethyldithiocarbamoyl zinc ethylene bisdithiocarbamate, bis(dimethylthiocarbamoyl) disulfide, the isomer of crotonic acid and 2,6-dinitro-4-octylphenyl and the like, or repellents such as, for example, dimethyl phthalate, 2,3,4,5-bis-(A2-butylene) tetrahydrofuran, 2,3,4,5-bis-($\Delta_2$-butylene)tetrahydrofurfuryl alcohol, N,N-diethyl-m-toluamide (termed "DEET" hereinbelow), caprylic acid, diethylamide, 2,3,4,5-bis($\Delta_2$-butylene)tetrahydrofurrural, di-n-propyl isocinchomeronate, sec-butyl styryl ketone, nonyl styryl ketone, n-propylacetanilide, 2-ethyl-1,3-hexanediol, di-n-butyl succinate, 2-butoxyethyl-2-furfurylidene acetate, dibutyl phthalate, tetrahydrothiophene, β-naphthol, diallyl sulfide, bis(dimethylthiocarbamoyl) disulfide and the like, rodent repellents such as, for example, tetramethylthiuram disulfide, guanidine, naphthalenecresol, cycloheximide, zinc dimethyldithiocarbamate, cyclohexylamine, N,N-dimethylsulphenyl dithiocarbamate, and the like, repellents for dogs and cats such as, for example, 2,6-dimethylocta-2,6-dien-8-al (termed "citral" hereinbelow), 0,0-diethyl S-2-ethylthioethyl dithiophosphate (termed "ETP" hereinbelow), 0,0-dimethyl S-2-isopropylthioethyl dithiophosphate (termed "M12P" hereinbelow) and the like, bird repellents such as, for example, chloralose, 4-(methylthio)-3,5-xylyl-N-methylcarbamate, 4-aminopyridinenthraquinone, tetramethylthiuram disulfide, diallyl disulfide and the like, rodenticides such as, for example, sodium monofluoroacetate, warfarin, coumachlor, fumarin, norbomid, N-3-pyridyl-methyl-N'-nitrophenylurea, α-naphthylthiourea, thiosemicarbazide, difenacoum, pival, chlorphacinon, cadciferol and the like.

The gel formulations according to the invention are preferably prepared using solvents. Diluents which can be used are virtually all inert organic solvents. These preferably include aliphatic and aromatic, optionally halogenated hydrocarbons such as penlane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulfoxide, tetramethylene sulfone, hexamethylphosphoric triamide and Shellsol T®.

The formulations generally comprise between 0.1 and 95% by weight of insecticidal active compound, preferably between 0.5 and 90% by weight.

The formulations furthermore generally comprise between 1 and 90% by weight of vaporization modifiers, preferably between 40 and 80% by weight, and generally between 1 and 8% by weight of gel formers, preferably between 3 and 6% by weight. The ratio of active compound/vaporization modifier in the insecticide-comprising gel formulations according to the invention is between 9 and 0.5, preferably 1. Preparation and use of the insecticide-comprising gel formulations according to the invention can be seen from the examples which follow.

It will be understood that the specification and examples are illustrative but not limitative of the present invention and that other embodiments within the spirit and scope of the invention will suggest themselves to those skilled in the art.

TABLE 1

| Example | Insecticide content | Gel former | Stabilizer | Volatilization modifier | Solvent |
|---|---|---|---|---|---|
| 1 | 39.5% Transfluthrin ® | 4% Aerosil 200 ® | 1% BHT | 55.5% Diphyl THT ® | — |
| 2 | 39.5% Transfluthrin ® | 6% Aerosil 200 ® | 1% BHT | 53.5% Diphyl THT ® | — |
| 3 | 23.8% Transfluthrin ® | 3.6% Aerosil 200 ® | 0.6% BHT | 32% Diphyl THT ® | 40% Shellsol T ® |

Example 1

The insecticide-comprising gel formulation of Example 1 is prepared as follows:

For a 100 kg batch, 39.5 kg of liquid Transfluthrin® (temperature approximately 40° C.) is introduced into a Bekumix stirring apparatus, 55 kg of Diphyl THT® and 1 kg of BHT are added, and the mixture is stirred until a clear solution has formed. It is possible to additionally stir into the formulation perfume oils, preferably aurantiol, citronella oil, $C_{10}$–$C_{16}$ aidehyde, birch tar oil, benzyl salicylate, lavender oil, rose oil in combination with or without the colorants Hostasol gelb 36®, Relolin-Brillantrot BLS®, 1,4-diaminoanthraquinone, Alizarin VK6/225®, Fettrot HRR®, Feltrot G®, Solvaperm Grtin®. 4 kg of Aerosil 200® are introduced in vacuo into the rapidly stirred clear solution until a gel has formed.

For use, the gel formulations, generally in mounts of 0.3–5 g, preferably in amounts of 0.3–3 g, depending on the use period, are packaged into thermoformed, deep-drawn or cast containers and sealed with polypropylene film. Preferred materials for the containers are aluminum, polyester, polyethylene, and metals. The container size is chosen such that the bottom area of the container has the same size as the heating area of the heating device and transfers temperatures from 70° to 110° C.

The controlled and sustained release of insecticidal active compounds is shown as follows by applying Example 1:

1.5 g of the insecticide-comprising gel formulation are distributed uniformly on the surface of a deep-drawn aluminum container of dimensions (4×2.5×0.4 cm) and sealed with a Walothen C50SE® PP film. In a heating device having a temperature of 100°–110° C., the container is heated for 8 hours per day, and the amounts of active compound released are determined. The evaporated mount of insecticide is:

1. determined gravimetrically by determining the amount of evaporated substance and analyzing the residue, and
2. analyzing the insecticide vapors released, with the aid of a specific apparatus: a funnel packed with silica gel is arranged directly above the heating device, absorbing the insecticide vapors released in a gentle, constant stream of air. The insecticide residues absorbed in the funnel are removed by washing with acetone, transferred into volumetric flasks and analyzed by means of gas chromatography to determine the degree of volatilization.

The results of the evaporation experiments are shown in Table 2.

The insecticide-comprising gel formulation of Example 1 is compared in each case with a sustained vapor-producing system as it is known from the prior art (GB 2 153 227). The results are shown in Table 3. Based on the results obtained, a use period of 60 days, which is preferred, can be achieved without problems.

The two formulations were then compared with each other in biological tests.

In sustained vapor-producing systems, the activity of the insecticide-comprising gel formulation of Example 1 in the above-tested system is markedly better than the activity of liquid formulations known already from the prior art.

TABLE 2

Evaporation rates
Heating temperature Example 1: 100–110° C. (invention)
Comparison: 130–140° C. (prior art)
Operating time: 8 hours per day

| | Amount of formulation in the vapor [mg/h] | | Amount of active compound in the vapor [mg/h] | |
|---|---|---|---|---|
| Days | Example 1 | Comparison | Example 1 | Comparison |
| 0 | 0 | 0 | 0 | 0 |
| 2 | 2.8 | 181 | 0.8 | 1.67 |
| 4 | 2.7 | 154 | 0.9 | 4.5 |
| 6 | 2.6 | 129 | 1.1 | 4.1 |
| 8 | 2.6 | 124 | 1.1 | 4 |
| 10 | 3.2 | 106 | 1.1 | 3.95 |
| 12 | 3.2 | 132 | 1.2 | 3.8 |
| 14 | 3.4 | 151 | 1.3 | 3.8 |
| 16 | 3.5 | 112 | 1.3 | 3.5 |
| 18 | 3.5 | 107 | 1.4 | 3.5 |
| 20 | 3.3 | 125 | 1.4 | 3.5 |
| 22 | 2.8 | 104 | 1.4 | 3.6 |
| 24 | 2.4 | 106 | 1.4 | 3.8 |
| 26 | 3.2 | 103 | 1.3 | 3.3 |
| 28 | 2.8 | 100 | 1.1 | 3.3 |
| 30 | 2.8 | 94 | 0.9 | 2.97 |
| 32 | 2.8 | 88 | 1.3 | 2.77 |
| 34 | 2.8 | 80 | 1.1 | 2.6 |
| 36 | 2.8 | 78 | 1.1 | 2.3 |
| 38 | 2.8 | 49 | 1.1 | 1.22 |
| 40 | 2.3 | 40 | 0.9 | 0.7 |

TABLE 3

Biological activity
Mosquito species: *Aedes aegypti*
Room size: 36 $m^3$
Type of room: 1 window open
Temperature: 20–25° C.
Heating temperature Example 1: 100–110° C. (invention)
Comparison: 130–140° C. (prior art)
Amount of formulation: Example 1: 1.5 g (invention)
Comparison: 36 g (prior art)

| | Operating time after start [hours] | Test level [cm] | Clinical death after hours and minutes 10% CD | 50% CD | 95% CD | 100% CD |
|---|---|---|---|---|---|---|
| Example 1 | 0 | 170 | 25' | 29' | 42' | 56' |
| | | 80 | 35' | 46' | 1h09' | 1h09' |
| | 8 | 170 | 22' | 27' | 33' | 38' |
| | | 80 | 27' | 37' | 54' | 59' |
| | 16 | 170 | 21' | 24' | 29' | 36' |
| | | 80 | 25' | 35' | 41' | 48' |
| Comparison | 0 | 170 | 54' | 1h06' | 1h25' | 1h31' |
| | | 80 | 56' | 1h11' | 1h38' | 1h52' |
| | 8 | 170 | 1h00' | 1h08' | 1h20' | 1h29' |
| | | 80 | 1h10' | 1h25' | 1h35' | 1h44' |
| | 16 | 170 | 55' | 1h00' | 1h10' | 1h12' |
| | | 80 | 1h00' | 1h10' | 1h20' | 1h27' |

A second experiment allowed the use period of 60 days of the insecticide-comprising gel formulation according to the present invention to be confirmed.

TABLE 4

Biological activity
Insecticidal action of the insecticide-comprising gel formulation according to the invention in vapor-producing systems
Mosquito species: *Aedes aegypti*
Room size: 36 $m^3$
Type of room: 1 window open
Temperature: 23–30° C.
Relative humidity in the room: 35–74%
Heating temperature: 100–110° C.
Active compound content: 39.5% of transfluthrin
Amount of formulation: 1.5 g

| | | Film container No. 1 | | | | Film container No. 2 | | | | Film container No. 3 | | | |
|---|---|---|---|---|---|---|---|---|---|---|---|---|---|
| Operating time/test | Number of mosquitoes | KD-action after minutes or hours | | % dead after | | KD-action after minutes or hours | | % dead after | | KD-action after minutes or hours | | % dead after | |
| after days (hours) | after hours | 50% | 100% | 9 h | 24 h | 50% | 100% | 9 h | 24 h | 50% | 100% | 9 h | 24 h |
| 0 days | 0 | 28' | 32' | 100 | 100 | 34' | 41' | 100 | 100 | 43' | 49' | 100 | 100 |
| | 1 | 5' | 6' | 100 | 100 | 5' | 7' | 100 | 100 | 5' | 7' | 100 | 100 |
| | 2 | 6' | 8' | 100 | 100 | 7' | 9' | 100 | 100 | 9' | 11' | 100 | 100 |
| | 3 | 9' | 11' | 100 | 100 | 10' | 16' | 100 | 100 | 13' | 17' | 100 | 100 |
| | 4 | 8' | 11' | 100 | 100 | 10' | 13' | 100 | 100 | 13' | 17' | 100 | 100 |
| | 5 | 7' | 9' | 100 | 100 | 8' | 11' | 100 | 100 | 12' | 17' | 100 | 100 |
| | 6 | 7' | 9' | 100 | 100 | 6' | 9' | 100 | 100 | 7' | 9' | 100 | 100 |
| | 7 | 5' | 7' | 100 | 100 | 7' | 8' | 100 | 100 | 7' | 9' | 100 | 100 |
| | 8 | 4' | 6' | 100 | 100 | 6' | 8' | 100 | 100 | 6' | 9' | 100 | 100 |
| 1 day (8 hours) | 0 | 35' | 40' | 100 | 100 | 30' | 35' | 100 | 100 | 38' | 43' | 100 | 100 |
| | 1 | 8' | 11' | 100 | 100 | 9' | 11' | 100 | 100 | 15' | 21' | 100 | 100 |
| | 2 | 5' | 7' | 100 | 100 | 5' | 7' | 100 | 100 | 10' | 13' | 100 | 100 |
| | 3 | 5' | 9' | 100 | 100 | 9' | 10' | 100 | 100 | 9' | 13' | 100 | 100 |
| | 4 | 5' | 8' | 100 | 100 | 6' | 9' | 100 | 100 | 6' | 10' | 100 | 100 |
| | 5 | 4' | 6' | 100 | 100 | 4' | 5' | 100 | 100 | 4' | 5' | 100 | 100 |
| | 6 | 4' | 6' | 100 | 100 | 3' | 5' | 100 | 100 | 4' | 6' | 100 | 100 |
| | 7 | 4' | 5' | 100 | 100 | 4' | 6' | 100 | 100 | 4' | 6' | 100 | 100 |
| | 8 | 3' | 5' | 100 | 100 | 3' | 5' | 100 | 100 | 3' | 5' | 100 | 100 |
| 2 days (16 hours) | 0 | 38' | 46' | 100 | 100 | 37' | 47' | 100 | 100 | 1h02' | 1h02' | 100 | 100 |
| | 1 | 17' | 26' | 100 | 100 | 15' | 23' | 100 | 100 | 35' | 42' | 100 | 100 |
| | 2 | 15' | 34' | 100 | 100 | 10' | 19' | 100 | 100 | 25' | 48' | 100 | 100 |
| | 3 | 12' | 24' | 100 | 100 | 10' | 18' | 100 | 100 | 16' | 32' | 100 | 100 |
| | 4 | 8' | 12' | 100 | 100 | 10' | 13' | 100 | 100 | 29' | 44' | 100 | 100 |

TABLE 4-continued

Biological activity
Insecticidal action of the insecticide-comprising gel formulation according to the invention in vapor-producing systems
Mosquito species: *Aedes aegypti*
Room size: 36 $m^3$
Type of room: 1 window open
Temperature: 23–30° C.
Relative humidity in the room: 35–74%
Heating temperature: 100–110° C.
Active compound content: 39.5% of transfluthrin
Amount of formulation: 1.5 g

| | | Film container No. 1 | | | | Film container No. 2 | | | | Film container No. 3 | | | |
|---|---|---|---|---|---|---|---|---|---|---|---|---|---|
| Operating time/test | Number of mosquitoes | KD-action after minutes or hours | | % dead after | | KD-action after minutes or hours | | % dead after | | KD-action after minutes or hours | | % dead after | |
| after days (hours) | after hours | 50% | 100% | 9 h | 24 h | 50% | 100% | 9 h | 24 h | 50% | 100% | 9 h | 24 h |
| | 5 | 9' | 14' | 100 | 100 | 8' | 12' | 100 | 100 | 18' | 29' | 100 | 100 |
| | 6 | 9' | 11' | 100 | 100 | 6' | 9' | 100 | 100 | 17' | 22' | 100 | 100 |
| | 7 | 8' | 10' | 100 | 100 | 7' | 11' | 100 | 100 | 9' | 13' | 100 | 100 |
| | 8 | 7' | 10' | 100 | 100 | 7' | 11' | 100 | 100 | 9' | 13' | 100 | 100 |
| 3 days | 0 | 42' | 51' | 100 | | 36' | 41' | 100 | | 45' | 53' | 100 | |
| (24 hours) | 1 | 19' | 31' | 100 | | 14' | 23' | 100 | | 20' | 41' | 100 | |
| | 2 | 11' | 15' | 100 | | 14' | 19' | 100 | | 23' | 43' | 100 | |
| | 3 | 8' | 11' | 100 | | 9' | 13' | 100 | | 8' | 11' | 100 | |
| | 4 | 8' | 11' | 100 | | 9' | 13' | 100 | | 13' | 17' | 100 | |
| | 5 | 7' | 10' | 100 | | 9' | 12' | 100 | | 11' | 14' | 100 | |
| | 6 | 7' | 10' | 100 | | 7' | 10' | 100 | | 9' | 13' | 100 | |
| | 7 | 7' | 10' | 100 | | 7' | 9' | 100 | | 8' | 12' | 100 | |
| | 8 | 6' | 9' | 100 | | 6' | 8' | 100 | | 8' | 11' | 100 | |
| 7 days | 0 | 29' | 36' | 100 | 100 | 28' | 33' | 100 | 100 | 36' | 45' | 100 | 100 |
| (56 hours) | 1 | 15' | 21' | 100 | 100 | 13' | 17' | 100 | 100 | 17' | 23' | 100 | 100 |
| | 2 | 11' | 15' | 100 | 100 | 10' | 12' | 100 | 100 | 12' | 16' | 100 | 100 |
| | 3 | 14' | 22' | 100 | 100 | 16' | 19' | 100 | 100 | 15' | 20' | 100 | 100 |
| | 4 | 13' | 19' | 100 | 100 | 14' | 18' | 100 | 100 | 12' | 16' | 100 | 100 |
| | 5 | 11' | 17' | 100 | 100 | 14' | 19' | 100 | 100 | 10' | 14' | 100 | 100 |
| | 6 | 12' | 18' | 100 | 100 | 16' | 21' | 100 | 100 | 11' | 15' | 100 | 100 |
| | 7 | 10' | 15' | 100 | 100 | 14' | 19' | 100 | 100 | 11' | 15' | 100 | 100 |
| | 8 | 12' | 18' | 100 | 100 | 13' | 18' | 100 | 100 | 15' | 18' | 100 | 100 |
| 14 days | 0 | 43' | 55' | 100 | 100 | 38' | 44' | 100 | 100 | 40' | 46' | 100 | 100 |
| (112 hours) | 1 | 25' | 37' | 100 | 100 | 19' | 26' | 100 | 100 | 23' | 30' | 100 | 100 |
| | 2 | 15' | 19' | 100 | 100 | 16' | 21' | 100 | 100 | 19' | 27' | 100 | 100 |
| | 3 | 14' | 21' | 100 | 100 | 18' | 25' | 100 | 100 | 21' | 29' | 100 | 100 |
| | 4 | 13' | 18' | 100 | 100 | 18' | 31' | 100 | 100 | 19' | 23' | 100 | 100 |
| | 5 | 12' | 19' | 100 | 100 | 16' | 23' | 100 | 100 | 26' | 37' | 100 | 100 |
| | 6 | 12' | 17' | 100 | 100 | 14' | 21' | 100 | 100 | 24' | 31' | 100 | 100 |
| | 7 | 10' | 16' | 100 | 100 | 12' | 17' | 100 | 100 | 20' | 27' | 100 | 100 |
| | 8 | 14' | 17' | 100 | 100 | 13' | 18' | 100 | 100 | 18' | 25' | 100 | 100 |
| 21 days | 0 | 26' | 32' | 100 | 100 | 28' | 33' | 100 | 100 | 27' | 32' | 100 | 100 |
| (168 hours) | 1 | 9' | 14' | 100 | 100 | 7' | 9' | 100 | 100 | 0' | 12' | 100 | 100 |
| | 2 | 6' | 9' | 100 | 100 | 6' | 8' | 100 | 100 | 5' | 8' | 100 | 100 |
| | 3 | 6' | 8' | 100 | 100 | 6' | 8' | 100 | 100 | 6' | 9' | 100 | 100 |
| | 4 | 5' | 7' | 100 | 100 | 5' | 7' | 100 | 100 | 4' | 6' | 100 | 100 |
| | 5 | 5' | 7' | 100 | 100 | 5' | 8' | 100 | 100 | 5' | 7' | 100 | 100 |
| | 6 | 6' | 8' | 100 | 100 | 6' | 8' | 100 | 100 | 6' | 9' | 100 | 100 |
| | 7 | 6' | 8' | 100 | 100 | 6' | 9' | 100 | 100 | 6' | 9' | 100 | 100 |
| | 8 | 7' | 10' | 100 | 100 | 6' | 8' | 100 | 100 | 8' | 10' | 100 | 100 |
| 28 days | 0 | 31' | 40' | 100 | 100 | 39' | 48' | 100 | 100 | 48' | 56' | 100 | 100 |
| (224 hours) | 1 | 7' | 11' | 100 | 100 | 9' | 13' | 100 | 100 | 12' | 15' | 100 | 100 |
| | 2 | 6' | 10' | 100 | 100 | 8' | 13' | 100 | 100 | 11' | 15' | 100 | 100 |
| | 3 | 6' | 9' | 100 | 100 | 10' | 14' | 100 | 100 | 8' | 12' | 100 | 100 |
| | 4 | 7' | 10' | 100 | 100 | 10' | 13' | 100 | 100 | 11' | 14' | 100 | 100 |
| | 5 | 7' | 11' | 100 | 100 | 9' | 12' | 100 | 100 | 10' | 15' | 100 | 100 |
| | 6 | 11' | 16' | 100 | 100 | 8' | 10' | 100 | 100 | 10' | 14' | 100 | 100 |
| | 7 | 9' | 14' | 100 | 100 | 8' | 10' | 100 | 100 | 11' | 15' | 100 | 100 |
| | 8 | 10' | 15' | 100 | 100 | 9' | 14' | 100 | 100 | 10' | 15' | 100 | 100 |
| 35 days | 0 | 24' | 28' | 100 | 100 | 22' | 26' | 100 | 100 | 21' | 27' | 100 | 100 |
| (280 hours) | 1 | 5' | 8' | 100 | 100 | 5' | 7' | 100 | 100 | 5' | 7' | 100 | 100 |
| | 2 | 4' | 5' | 100 | 100 | 3' | 6' | 100 | 100 | 3' | 6' | 100 | 100 |
| | 3 | 3' | 5' | 100 | 100 | 3' | 5' | 100 | 100 | 3' | 5' | 100 | 100 |
| | 4 | 4' | 6' | 100 | 100 | 4' | 6' | 100 | 100 | 4' | 7' | 100 | 100 |
| | 5 | 6' | 10' | 100 | 100 | 8' | 13' | 100 | 100 | 8' | 12' | 100 | 100 |
| | 6 | 7' | 13' | 100 | 100 | 9' | 15' | 100 | 100 | 7' | 12' | 100 | 100 |
| | 7 | 8' | 45' | 100 | 100 | 14' | 44' | 100 | 100 | 9' | 37' | 100 | 100 |
| | 8 | 14' | 48' | 100 | 100 | 14' | 45' | 100 | 100 | 17' | 54' | 100 | 100 |
| 42 days | 0 | 30' | 36' | 100 | 100 | 35' | 41' | 100 | 100 | 36' | 44' | 100 | 100 |
| (336 hours) | 1 | 7' | 9' | 100 | 100 | 7' | 10' | 100 | 100 | 7' | 10' | 100 | 100 |

TABLE 4-continued

Biological activity
Insecticidal action of the insecticide-comprising gel formulation according to the invention in vapor-producing systems
Mosquito species: *Aedes aegypti*
Room size: 36 $m^3$
Type of room: 1 window open
Temperature: 23–30° C.
Relative humidity in the room: 35–74%
Heating temperature: 100–110° C.
Active compound content: 39.5% of transfluthrin
Amount of formulation: 1.5 g

| | | Film container No. 1 | | | | Film container No. 2 | | | | Film container No. 3 | | | |
|---|---|---|---|---|---|---|---|---|---|---|---|---|---|
| Operating time/test | Number of mosquitoes | KD-action after minutes or hours | | % dead after | | KD-action after minutes or hours | | % dead after | | KD-action after minutes or hours | | % dead after | |
| after days (hours) | after hours | 50% | 100% | 9 h | 24 h | 50% | 100% | 9 h | 24 h | 50% | 100% | 9 h | 24 h |
| | 2 | 7' | 9' | 100 | 100 | 7' | 9' | 100 | 100 | 8' | 11' | 100 | 100 |
| | 3 | 7' | 10' | 100 | 100 | 6' | 8' | 100 | 100 | 7' | 10' | 100 | 100 |
| | 4 | 10' | 13' | 100 | 100 | 11' | 14' | 100 | 100 | 10' | 13' | 100 | 100 |
| | 5 | 11' | 14' | 100 | 100 | 12' | 16' | 100 | 100 | 7' | 11' | 100 | 100 |
| | 6 | 6' | 10' | 100 | 100 | 7' | 12' | 100 | 100 | 6' | 10' | 100 | 100 |
| | 7 | 9' | 13' | 100 | 100 | 7' | 10' | 100 | 100 | 7' | 12' | 100 | 100 |
| | 8 | 8' | 12' | 100 | 100 | 7' | 9' | 100 | 100 | 7' | 11' | 100 | 100 |
| 49 days | 0 | 26' | 36' | 100 | 100 | 34' | 47' | 100 | 100 | 27' | 38' | 100 | 100 |
| (392 hours) | 1 | 8' | 12' | 100 | 100 | 9' | 12' | 100 | 100 | 7' | 10' | 100 | 100 |
| | 2 | 8' | 12' | 100 | 100 | 7' | 11' | 100 | 100 | 7' | 10' | 100 | 100 |
| | 3 | 8' | 11' | 100 | 100 | 7' | 10' | 100 | 100 | 6' | 10' | 100 | 100 |
| | 4 | 8' | 11' | 100 | 100 | 7' | 11' | 100 | 100 | 6' | 9' | 100 | 100 |
| | 5 | 6' | 9' | 100 | 100 | 8' | 12' | 100 | 100 | 5' | 8' | 100 | 100 |
| | 6 | 5' | 9' | 100 | 100 | 8' | 12' | 100 | 100 | 8' | 11' | 100 | 100 |
| | 7 | 8' | 10' | 100 | 100 | 10' | 16' | 100 | 100 | 7' | 11' | 100 | 100 |
| | 8 | 9' | 12' | 100 | 100 | 11' | 16' | 100 | 100 | 9' | 12' | 100 | 100 |
| 56 days | 0 | 40' | 49' | 100 | 100 | 30' | 35' | 100 | 100 | 36' | 43' | 100 | 100 |
| (448 hours) | 1 | 16' | 21' | 100 | 100 | 15' | 22' | 100 | 100 | 14' | 20' | 100 | 100 |
| | 2 | 9' | 12' | 100 | 100 | 12' | 15' | 100 | 100 | 8' | 12' | 100 | 100 |
| | 3 | 9' | 12' | 100 | 100 | 9' | 12' | 100 | 100 | 9' | 13' | 100 | 100 |
| | 4 | 8' | 11' | 100 | 100 | 10' | 13' | 100 | 100 | 8' | 11' | 100 | 100 |
| | 5 | 8' | 11' | 100 | 100 | 9' | 13' | 100 | 100 | 7' | 10' | 100 | 100 |
| | 6 | 8' | 12' | 100 | 100 | 9' | 13' | 100 | 100 | 10' | 13' | 100 | 100 |
| | 7 | 9' | 14' | 100 | 100 | 10' | 15' | 100 | 100 | 11' | 16' | 100 | 100 |
| | 8 | 12' | 15' | 100 | 100 | 11' | 14' | 100 | 100 | 13' | 18' | 100 | 100 |
| 63 days | 0 | 37' | 51' | 100 | 100 | 36' | 50' | 100 | 100 | 46' | 56' | 100 | 100 |
| (504 hours) | 1 | 11' | 14' | 100 | 100 | 16' | 21' | 100 | 100 | 19' | 23' | 100 | 100 |
| | 2 | 9' | 12' | 100 | 100 | 11' | 14' | 100 | 100 | 16' | 22' | 100 | 100 |
| | 3 | 10' | 13' | 100 | 100 | 12' | 17' | 100 | 100 | 14' | 20' | 100 | 100 |
| | 4 | 9' | 12' | 100 | 100 | 12' | 16' | 100 | 100 | 10' | 14' | 100 | 100 |
| | 5 | 7' | 10' | 100 | 100 | 11' | 14' | 100 | 100 | 8' | 13' | 100 | 100 |
| | 6 | 8' | 11' | 100 | 100 | 9' | 13' | 100 | 100 | 7' | 12' | 100 | 100 |
| | 7 | 7' | 10' | 100 | 100 | 8' | 11' | 100 | 100 | 8' | 11' | 100 | 100 |
| | 8 | 9' | 12' | 100 | 100 | 9' | 13' | 100 | 100 | 10' | 12' | 100 | 100 |
| 69 days | 0 | 46' | 1h01" | 100 | 100 | 33' | 48' | 100 | 100 | 45' | 1h03' | 100 | 100 |
| (552 hours) | 1 | 15' | 21' | 100 | 100 | 14' | 20' | 100 | 100 | 20' | 24' | 100 | 100 |
| | 2 | 13' | 15' | 100 | 100 | 12' | 16' | 100 | 100 | 14' | 18' | 100 | 100 |
| | 3 | 10' | 13' | 100 | 100 | 12' | 15' | 100 | 100 | 15' | 19' | 100 | 100 |
| | 4 | 10' | 13' | 100 | 100 | 11' | 14' | 100 | 100 | 18' | 23' | 100 | 100 |
| | 5 | 12' | 16' | 100 | 100 | 11' | 15' | 100 | 100 | 17' | 21' | 100 | 100 |
| | 6 | 10' | 14' | 100 | 100 | 10' | 14' | 100 | 100 | 13' | 19' | 100 | 100 |
| | 7 | 8' | 11' | 100 | 100 | 8' | 11' | 100 | 100 | 10' | 14' | 100 | 100 |
| | 8 | 9' | 11' | 100 | 100 | 8' | 11' | 100 | 100 | 11' | 17' | 100 | 100 |
| 76 days | 0 | 50' | 1h01' | 100 | 100 | 48' | 58' | 100 | 100 | 50' | 1h05' | 100 | 100 |
| (608 hours) | 1 | 11' | 15' | 100 | 100 | 13' | 18' | 100 | 100 | 22' | 34' | 100 | 100 |
| | 2 | 9' | 13' | 100 | 100 | 11' | 15' | 100 | 100 | 17' | 23' | 100 | 100 |
| | 3 | 10' | 13' | 100 | 100 | 11' | 14' | 100 | 100 | 13' | 19' | 100 | 100 |
| | 4 | 8' | 13' | 100 | 100 | 12' | 15' | 100 | 100 | 16' | 23' | 100 | 100 |
| | 5 | 7' | 11' | 100 | 100 | 11' | 13' | 100 | 100 | 8' | 11' | 100 | 100 |
| | 6 | 6' | 10' | 100 | 100 | 10' | 15' | 100 | 100 | 9' | 13' | 100 | 100 |
| | 7 | 6' | 9' | 100 | 100 | 9' | 13' | 100 | 100 | 11' | 16' | 100 | 100 |
| | 8 | 5' | 8' | 100 | 100 | 7' | 9' | 100 | 100 | 8' | 13' | 100 | 100 |
| 84 days | 0 | 49' | 1h00' | 100 | 100 | Experiment aborted - faulty timer | | | | 1h05' | 1h20' | 100 | 100 |
| (672 hours) | 1 | 16' | 22' | 100 | 100 | | | | | 28' | 36' | 100 | 100 |
| | 2 | 16' | 24' | 100 | 100 | | | | | 24' | 31' | 100 | 100 |
| | 3 | 15' | 26' | 100 | 100 | | | | | 11' | 22' | 100 | 100 |
| | 4 | 18' | 32' | 100 | 100 | | | | | 16' | 30' | 100 | 100 |
| | 5 | 12' | 25' | 100 | 100 | | | | | 15' | 25' | 100 | 100 |
| | 6 | 11' | 23' | 100 | 100 | | | | | 14' | 26' | 100 | 100 |
| | 7 | 10' | 14' | 100 | 100 | | | | | 15' | 22' | 100 | 100 |

TABLE 4-continued

Biological activity
Insecticidal action of the insecticide-comprising gel formulation according to the invention in vapor-producing systems
Mosquito species: *Aedes aegypti*
Room size: 36 $m^3$
Type of room: 1 window open
Temperature: 23–30° C.
Relative humidity in the room: 35–74%
Heating temperature: 100–110° C.
Active compound content: 39.5% of transfluthrin
Amount of formulation: 1.5 g

| | | Film container No. 1 | | | | Film container No. 2 | | | | Film container No. 3 | | | |
|---|---|---|---|---|---|---|---|---|---|---|---|---|---|
| Operating time/test | Number of mosquitoes | KD-action after minutes or hours | | % dead after | | KD-action after minutes or hours | | % dead after | | KD-action after minutes or hours | | % dead after | |
| after days (hours) | after hours | 50% | 100% | 9 h | 24 h | 50% | 100% | 9 h | 24 h | 50% | 100% | 9 h | 24 h |
| | 8 | 10' | 14' | 100 | 100 | | | | | 11' | 16' | 100 | 100 |
| 91 days | 0 | 41' | 1h20' | 100 | 100 | | | | | 41' | 1h18h | 100 | 100 |
| (728 hours) | 1 | 29' | 1h14' | 100 | 100 | | | | | 33' | 48' | 100 | 100 |
| | 2 | 22' | 38' | 100 | 100 | | | | | 17' | 22' | 100 | 100 |
| | 3 | 20' | 28' | 100 | 100 | | | | | 18' | 25' | 100 | 100 |
| | 4 | 18' | 26' | 100 | 100 | | | | | 16' | 22' | 100 | 100 |
| | 5 | 29' | 42' | 100 | 100 | | | | | 21' | 29' | 100 | 100 |
| | 6 | 20' | 28' | 100 | 100 | | | | | 20' | 28' | 100 | 100 |
| | 7 | 20' | 29' | 100 | 100 | | | | | 18' | 29' | 100 | 100 |
| | 8 | 20' | 27' | 100 | 100 | | | | | 20' | 28' | 100 | 100 |

TABLE 5

Biological activity
Insecticidal action of the insecticide-comprising gel formulation according to the invention in vapor-producing systems
Mosquito species: *Culex quinquefasciatus*
Room size: 36 $m^3$
Type of room: 1 window open
Temperature: 23–30° C.
Relative humidity in the room: 35–74%
Heating temperature: 100–110° C.
Active compound content: 39.5% of transfluthrin
Amount of formulation: 1.5 g

| | | Film container No. 1 | | | | Film container No. 2 | | | | Film container No. 3 | | | |
|---|---|---|---|---|---|---|---|---|---|---|---|---|---|
| Operating time/test | Number of mosquitoes | KD-action after minutes or hours | | % dead after | | KD-action after minutes or hours | | % dead after | | KD-action after minutes or hours | | % dead after | |
| after days (hours) | after hours | 50% | 100% | 9 h | 24 h | 50% | 100% | 9 h | 24 h | 50% | 100% | 9 h | 24 h |
| 0 days | 0 | 1h23' | 2h58' | 100 | 100 | 2h10' | 4h08' | 100 | 100 | 2h54' | 4h17' | 100 | 100 |
| | 1 | 1h12' | 2h19' | 100 | 100 | 1h45' | 3h18' | 100 | 100 | 2h03' | 3h18' | 100 | 100 |
| | 2 | 1h27' | 3h15' | 100 | 100 | 2h05' | 3h09' | 100 | 100 | 2h30' | 3h43' | 100 | 100 |
| | 3 | 2h0.5' | 3h13' | 100 | 100 | 2h23' | 3h18' | 100 | 100 | 2h45' | 4h20' | 100 | 100 |
| | 4 | 1h43' | 2h33' | 100 | 100 | 1h48' | 3h08' | 100 | 100 | 2h30' | 3h55' | 100 | 100 |
| | 5 | 1h18' | 2h18' | 100 | 100 | 1h13' | 2h25' | 100 | 100 | 2h33' | — | 90 | 95 |
| | 6 | 1h02' | 2h05' | 100 | 100 | 1h12' | 2h19' | 100 | 100 | 2h08' | — | 90 | 93 |
| | 7 | 1h10' | — | 75 | 83 | 58' | — | 75 | 78 | — | — | 43 | 40 |
| | 8 | — | — | 0 | 5 | — | — | 0 | 5 | — | — | 0 | 0 |
| 1 day | 0 | 3h08' | 4h20' | 100 | 100 | 4h15' | 5h40' | 100 | 100 | 5h50' | — | 88 | 95 |
| (8 hours) | 1 | 1h53' | 3h23' | 100 | 100 | 2h18' | 4h13' | 100 | 100 | 4h28' | 6h10' | 100 | 100 |
| | 2 | 1h45' | 2h55' | 100 | 100 | 2h18' | 3h45' | 100 | 100 | 6h05' | — | 70 | 100 |
| | 3 | 2h05' | 3h23' | 100 | 100 | 2h05' | 3h43' | 100 | 100 | 3h40' | — | 90 | 100 |
| | 4 | 2h18' | — | 95 | 98 | 1h20' | 2h15' | 100 | 100 | 3h30' | — | 73 | 100 |
| | 5 | 2h10' | — | 90 | 98 | 1h25' | 2h13' | 100 | 100 | 3h05' | — | 73 | 98 |
| | 6 | 1h15' | — | 83 | 98 | 1h15' | 1h50' | 100 | 100 | 1h50' | — | 83 | 95 |
| | 7 | — | — | 5 | 58 | 40' | — | 75 | 98 | — | — | 25 | 43 |
| | 8 | — | — | 0 | 0 | — | — | 0 | 0 | — | — | 0 | 0 |
| 2 days | 0 | 5h10' | — | 90 | 90 | 4h38' | 7h18' | 100 | 100 | — | — | 18 | 33 |
| (16 hours) | 1 | 5h03' | — | 90 | 95 | 5h00' | — | 88 | 100 | — | — | 0 | 15 |
| | 2 | 4h35' | — | 73 | 78 | 6h10' | — | 63 | 95 | — | — | 0 | 15 |
| | 3 | 4h50' | — | 70 | 75 | 3h08' | — | 90 | 100 | — | — | 0 | 10 |
| | 4 | 3h30' | — | 60 | 75 | 3h40' | — | 75 | 93 | — | — | 0 | 10 |
| | 5 | — | — | 20 | 38 | — | — | 45 | 78 | — | — | 0 | 0 |
| | 6 | — | — | 0 | 5 | — | — | 5 | 10 | — | — | 0 | 0 |

TABLE 5-continued

Biological activity
Insecticidal action of the insecticide-comprising gel formulation according to the invention in vapor-producing systems
Mosquito species: *Culex quinquefasciatus*
Room size: 36 $m^3$
Type of room: 1 window open
Temperature: 23–30° C.
Relative humidity in the room: 35–74%
Heating temperature: 100–110° C.
Active compound content: 39.5% of transfluthrin
Amount of formulation: 1.5 g

| Operating time/test | Number of mosquitoes | Film container No. 1 | | | | Film container No. 2 | | | | Film container No. 3 | | | |
|---|---|---|---|---|---|---|---|---|---|---|---|---|---|
| | | KD-action after minutes or hours | | % dead after | | KD-action after minutes or hours | | % dead after | | KD-action after minutes or hours | | % dead after | |
| after days (hours) | after hours | 50% | 100% | 9 h | 24 h | 50% | 100% | 9 h | 24 h | 50% | 100% | 9 h | 24 h |
| | 7 | — | — | 0 | 0 | — | — | 0 | 0 | — | — | 0 | 0 |
| | 8 | — | — | 0 | 0 | — | — | 0 | 0 | — | — | 0 | 0 |
| 3 days | 0 | 3h18' | 4h47' | 100 | | 5h13' | 6h25' | 100 | | 6h00' | — | 90 | |
| (24 hours) | 1 | 2h29' | 3h48' | 100 | | 3h00' | 4h25' | 100 | | 5h38' | 6h33' | 100 | |
| | 2 | 2h33' | 3h48' | 100 | | 4h04' | 5h00' | 100 | | 4h38' | — | 78 | |
| | 3 | 2h07' | 4h00' | 100 | | 2h44' | 3h33' | 100 | | 3h50' | — | 88 | |
| | 4 | 2h08' | 3h29' | 100 | | 2h40' | 3h23' | 100 | | >4h | — | 80 | |
| | 5 | 1h47' | 2h30' | 100 | | 1h53' | 2h27' | 100 | | — | — | 60 | |
| | 6 | 1h30' | 2h08' | 100 | | 1h32' | 2h14' | 100 | | — | — | 45 | |
| | 7 | 1h28' | — | 53 | | 48' | — | 80 | | — | — | 23 | |
| | 8 | — | — | 0 | | — | — | — | | — | — | 0 | |
| 7 days | 0 | 2h33' | 6h18' | 100 | 100 | 3h55' | 6h23' | 100 | 98 | 3h08' | 4h43 | 100 | 100 |
| (56 hours) | 1 | 2h53' | — | 95 | 100 | 3h10' | — | 95 | 98 | 2h48' | 4h43' | 100 | 100 |
| | 2 | 3h45' | — | 90 | 93 | 3h08' | — | 98 | 98 | 2h50' | 2h38' | 100 | 100 |
| | 3 | 3h40' | — | 83 | 98 | 3h25' | — | 78 | 98 | 2h55' | 3h48' | 100 | 100 |
| | 4 | 3h05' | — | 83 | 95 | 3h25' | — | 80 | 93 | 2h10' | 3h55' | 100 | 98 |
| | 5 | 2h15 | — | 90 | 95 | — | — | 30 | 83 | 1h33' | — | 98 | 100 |
| | 6 | — | — | 40 | 98 | — | — | 33 | 63 | 1h28' | — | 95 | 98 |
| | 7 | — | — | 38 | 78 | — | — | 10 | 33 | — | — | 43 | 95 |
| | 8 | — | — | 8 | 48 | — | — | 10 | 13 | — | — | 10 | 23 |
| 14 days | 0 | 4h20' | 6h45' | 100 | 100 | 5h35' | — | 98 | 98 | 3h50' | 5h45' | 100 | 100 |
| (112 hours) | 1 | 3h40' | 6h20' | 100 | 100 | 5h10' | — | 95 | 100 | 4h10' | 6h00' | 100 | 100 |
| | 2 | 3h10' | — | 88 | 100 | 3h43' | — | 93 | 100 | 3h30' | 5h03' | 100 | 100 |
| | 3 | 3h15' | — | 73 | 100 | 4h15' | — | 70 | 100 | 3h30' | — | 88 | 100 |
| | 4 | 2h55' | — | 80 | 100 | 2h55' | — | 75 | 95 | 3h13' | — | 58 | 100 |
| | 5 | 2h15' | — | 73 | 95 | — | — | 38 | 85 | 2h00' | — | 73 | 98 |
| | 6 | — | — | 28 | 88 | — | — | 25 | 70 | >3h | — | 58 | 88 |
| | 7 | — | — | 8 | 43 | — | — | 13 | 28 | — | — | 10 | 68 |
| | 8 | — | — | 3 | 3 | — | — | 3 | 10 | — | — | 3 | 13 |
| 21 days | 0 | 1h53' | 2h33' | 100 | 100 | 1h50' | 2h23' | 100 | 100 | 1h50' | 2h08' | 100 | 100 |
| (168 hours) | 1 | 1h27' | 1h53' | 100 | 100 | 1h28' | 1h53' | 100 | 100 | 1h15' | 1h48' | 100 | 100 |
| | 2 | 53' | 1h19' | 100 | 100 | 51' | 1h12' | 100 | 100 | 1h06' | 1h31' | 100 | 100 |
| | 3 | 40' | 55' | 100 | 100 | 38' | 47' | 100 | 100 | 51' | 1h09' | 100 | 100 |
| | 4 | 37' | 1h03' | 100 | 100 | 34' | 1h02' | 100 | 100 | 36' | 1h04' | 100 | 100 |
| | 5 | 2h00' | — | 88 | 85 | 1h25' | 2h24' | 98 | 98 | 58' | 1h42' | 100 | 100 |
| | 6 | — | — | 40 | 48 | — | — | 43 | 60 | — | — | 45 | 85 |
| | 7 | — | — | 0 | 5 | — | — | 0 | 5 | — | — | 8 | 25 |
| | 8 | — | — | 0 | 0 | — | — | 0 | 0 | — | — | 0 | 5 |
| 28 days | 0 | 1h55' | 2h15' | 100 | 100 | 1h53' | 2h15' | 100 | 100 | 2h13' | 2h35' | 100 | 100 |
| (224 hours) | 1 | 1h25' | 2h23' | 100 | 100 | 1h05' | 1h40' | 100 | 100 | 1h25' | 2h00' | 100 | 100 |
| | 2 | 1h30' | 2h40' | 100 | 100 | 48' | 1h38' | 100 | 100 | 1h03' | 2h05' | 100 | 100 |
| | 3 | 1h33' | 2h03' | 100 | 100 | 1h00' | 1h43' | 100 | 100 | 1h13' | 2h28' | 100 | 100 |
| | 4 | 1h28' | 2h08' | 100 | 100 | 1h15' | 2h05' | 100 | 100 | 1h20' | 2h00' | 100 | 100 |
| | 5 | 1h38' | 2h35' | 100 | 100 | 1h05' | 1h54' | 100 | 100 | 1h05' | 2h05' | 100 | 100 |
| | 6 | 1h20' | — | 95 | 100 | 50' | — | 98 | 100 | 1h03' | — | 98 | 100 |
| | 7 | 1h23' | — | 78 | 100 | 50' | — | 93 | 100 | 1h13' | — | 93 | 100 |
| | 8 | — | — | 25 | 63 | — | — | 45 | 78 | — | — | 10 | 100 |
| 35 days | 0 | 2h08' | 2h54' | 100 | 100 | 1h45' | 2h29' | 100 | 100 | 2h04' | 2h47' | 100 | 100 |
| (280 hours) | 1 | 1h10' | 1h33' | 100 | 100 | 1h11' | 1h48' | 100 | 100 | 1h20' | 2h10' | 100 | 100 |
| | 2 | 54' | 1h29' | 100 | 100 | 39' | 1h14' | 100 | 100 | 37' | 1h15' | 100 | 100 |
| | 3 | 48' | 1h09' | 100 | 100 | 50' | 1h40' | 100 | 100 | 37' | 1h14' | 100 | 100 |
| | 4 | >5h | — | 58 | 65 | 1h18' | — | 93 | 100 | 51' | — | 98 | 100 |
| | 5 | — | — | 35 | 28 | — | — | 48 | 75 | >4h | — | 55 | 58 |
| | 6 | — | — | 0 | 0 | — | — | 0 | 0 | — | — | 0 | 0 |
| | 7 | — | — | 0 | 0 | — | — | 0 | 0 | — | — | 0 | 0 |
| | 8 | — | — | 0 | 0 | — | — | 0 | 0 | — | — | 0 | 0 |
| 42 days | 0 | 2h10' | 3h25' | 100 | 100 | 1h55' | 2h30' | 100 | 100 | 1h09' | 1h43' | 100 | 100 |
| (336 hours) | 1 | 1h53' | 2h53' | 100 | 100 | 1h15' | 1h58' | 100 | 100 | 1h00' | 1h28' | 100 | 100 |
| | 2 | 1h08' | 2h33' | 100 | 100 | 1h08' | 2h05' | 100 | 100 | 48' | 1h25' | 100 | 100 |
| | 3 | 1h10' | 1h58' | 100 | 100 | 55' | 1h35' | 100 | 100 | 43' | 1h08' | 100 | 100 |

TABLE 5-continued

Biological activity
Insecticidal action of the insecticide-comprising gel formulation according to the invention in vapor-producing systems
Mosquito species: *Culex quinquefasciatus*
Room size: 36 $m^3$
Type of room: 1 window open
Temperature: 23–30° C.
Relative humidity in the room: 35–74%
Heating temperature: 100–110° C.
Active compound content: 39.5% of transfluthrin
Amount of formulation: 1.5 g

| Operating time/test | Number of mosquitoes | Film container No. 1 | | | | Film container No. 2 | | | | Film container No. 3 | | | |
|---|---|---|---|---|---|---|---|---|---|---|---|---|---|
| | | KD-action after minutes or hours | | % dead after | | KD-action after minutes or hours | | % dead after | | KD-action after minutes or hours | | % dead after | |
| after days (hours) | after hours | 50% | 100% | 9 h | 24 h | 50% | 100% | 9 h | 24 h | 50% | 100% | 9 h | 24 h |
| | 4 | 58' | 1h23' | 100 | 100 | 48' | 1h13' | 100 | 100 | 41' | 55' | 100 | 100 |
| | 5 | 51' | 1h19' | 100 | 100 | 55' | 1h20' | 100 | 100 | 27' | 1h05' | 100 | 100 |
| | 6 | 47' | 1h06' | 100 | 100 | 59' | 1h27' | 100 | 100 | 28' | 1h03' | 100 | 100 |
| | 7 | 50' | — | 68 | 85 | 48' | — | 90 | 93 | 26' | 53' | 100 | 98 |
| | 8 | — | — | 38 | 13 | — | — | 40 | 15 | — | — | 20 | 58 |
| 49 days | 0 | 2h09' | 3h25' | 100 | 100 | 1h58' | 3h08' | 100 | 100 | 52' | 1h18' | 100 | 100 |
| (392 hours) | 1 | 1h50' | 2h45' | 100 | 98 | 1h28' | 2h18' | 100 | 100 | 42' | 1h11' | 100 | 100 |
| | 2 | 1h18' | 2h08' | 100 | 100 | 1h08' | 2h00' | 100 | 100 | 43' | 1h00' | 100 | 100 |
| | 3 | 1h00' | 1h55' | 100 | 100 | 1h05' | 3h13' | 100 | 100 | 26' | 1h03' | 100 | 100 |
| | 4 | 52' | 1h46' | 100 | 100 | 58' | 2h09' | 100 | 95 | 19' | 46' | 100 | 100 |
| | 5 | 39' | — | 98 | 98 | 55' | 1h57' | 100 | 100 | 22' | 48 | 100 | 100 |
| | 6 | 55' | — | 98 | 93 | 42' | — | 93 | 90 | 48' | 1h06' | 100 | 100 |
| | 7 | — | — | 20 | 38 | — | — | 13 | 33 | — | — | 45 | 88 |
| | 8 | — | — | 3 | 13 | — | — | 3 | 15 | — | — | 20 | 48 |
| 56 days | 0 | 1h58' | 2h29' | 100 | 100 | 1h48' | 2h15' | 100 | 100 | 1h50' | 2h32' | 100 | 100 |
| (448 hours) | 1 | 1h21' | 2h05' | 100 | 100 | 1h07' | 2h03' | 100 | 100 | 1h25' | 2h00' | 100 | 100 |
| | 2 | 55' | 1h28' | 100 | 100 | 55' | 2h29' | 100 | 100 | 51' | 1h48' | 100 | 100 |
| | 3 | 59' | 2h01' | 100 | 100 | 1h14' | 1h57' | 100 | 100 | 53' | 1h18' | 100 | 100 |
| | 4 | 50' | 1h27' | 100 | 100 | 1h04' | 2h02' | 100 | 100 | 32' | 1h00' | 100 | 100 |
| | 5 | 49' | 1h15 | 100 | 100 | 1h02' | 2h08' | 100 | 100 | 28' | 49' | 100 | 100 |
| | 6 | 58' | — | 98 | 98 | 53' | — | 98 | 100 | 41' | 1h07' | 100 | 100 |
| | 7 | 51' | — | 85 | 95 | 1h00' | — | 65 | 90 | 50' | — | 85 | 100 |
| | 8 | — | — | 20 | 30 | — | — | 10 | 30 | — | — | 13 | 90 |
| 63 days | 0 | 2h05' | 3h00' | 100 | 100 | 3h30' | 5h08' | 100 | 100 | 1h58' | 3h25' | 100 | 100 |
| (504 hours) | 1 | 1h25' | 2h28' | 100 | 100 | 2h45' | 4h14' | 100 | 100 | 1h52' | 2h45' | 100 | 100 |
| | 2 | 58' | 2h03' | 100 | 100 | 2h05' | 2h55' | 100 | 100 | 1h08' | 2h03' | 100 | 100 |
| | 3 | 1h00' | 1h38' | 100 | 100 | 1h55' | 3h18' | 100 | 100 | 55' | 1h40' | 100 | 100 |
| | 4 | 32' | 1h10' | 100 | 100 | 1h45' | 2h58' | 100 | 98 | 42' | 1h13' | 100 | 100 |
| | 5 | 35' | 1h05' | 100 | 100 | 1h10' | 2h33' | 100 | 93 | 39' | 1h20 | 100 | 100 |
| | 6 | 24' | — | 98 | 100 | 1h00' | — | 95 | 73 | 45' | — | 98 | 100 |
| | 7 | 30' | — | 73 | 85 | 53' | — | 70 | 63 | — | — | 43 | 88 |
| | 8 | — | — | 0 | 3 | — | — | 3 | 10 | — | — | 3 | 13 |
| 69 days | 0 | 5h50' | — | 80 | 93 | 6h40' | — | 78 | 85 | 7h03' | — | 75 | 88 |
| (552 hours) | 1 | 5h35' | — | 85 | 93 | 5h53' | — | 75 | 93 | 6h58' | — | 65 | 93 |
| | 2 | 4h38' | — | 73 | 100 | 5h43' | — | 78 | 95 | 5h40' | — | 78 | 93 |
| | 3 | 4h23 | — | 75 | 95 | — | — | 45 | 90 | 5h15' | — | 60 | 95 |
| | 4 | — | — | 13 | 85 | — | — | 18 | 78 | — | — | 30 | 78 |
| | 5 | — | — | 13 | 75 | — | — | 15 | 75 | — | — | 13 | 33 |
| | 6 | — | — | 13 | 63 | — | — | 0 | 38 | — | — | 5 | 23 |
| | 7 | — | — | 0 | 30 | — | — | 0 | 13 | — | — | 0 | 5 |
| | 8 | — | — | 0 | 0 | — | — | 0 | 0 | — | — | 0 | 0 |
| 74 days | 0 | 6h10' | — | 95 | 95 | 7h40' | — | 68 | 80 | 6h08' | 7h58' | 98 | 100 |
| (608 hours) | 1 | 4h55' | — | 90 | 88 | 5h43' | — | 80 | 90 | 5h05' | — | 95 | 100 |
| | 2 | 4h13' | — | 80 | 93 | 4h45' | — | 75 | 73 | 4h00' | — | 95 | 98 |
| | 3 | 3h25' | — | 80 | 83 | 4h20' | — | 68 | 88 | 3h18' | 5h08' | 98 | 100 |
| | 4 | 3h45' | — | 68 | 88 | >5h | — | 55 | 60 | 2h50' | 3h38' | 98 | 95 |
| | 5 | >4h– | — | 50 | 58 | — | — | 48 | 53 | 2h05' | — | 80 | 95 |
| | 6 | — | — | 18 | 28 | — | — | 8 | 13 | >3h | — | 60 | 73 |
| | 7 | — | — | 5 | 20 | — | — | 3 | 0 | — | — | 33 | 40 |
| | 8 | — | — | 3 | 5 | — | — | 0 | 0 | — | — | 0 | 0 |
| 84 days | 0 | 4h40' | — | 95 | 95 | Experiment aborted - faulty timer | | | | — | — | 30 | 45 |
| (672 hours) | 1 | 4h23' | 7h48' | 100 | 100 | | | | | — | — | 38 | 50 |
| | 2 | 5h00' | — | 93 | 95 | | | | | — | — | 13 | 35 |
| | 3 | 4h18' | — | 75 | 88 | | | | | — | — | 5 | 28 |
| | 4 | 3h30' | — | 70 | 73 | | | | | — | — | 5 | 25 |
| | 5 | — | — | 8 | 20 | | | | | — | — | 5 | 10 |
| | 6 | — | — | 5 | 28 | | | | | — | — | 3 | 10 |
| | 7 | — | — | 3 | 5 | | | | | — | — | 0 | 10 |
| | 8 | — | — | 0 | 0 | | | | | — | — | 0 | 5 |
| 91 days | 0 | — | — | 13 | 33 | | | | | — | — | 40 | 48 |

TABLE 5-continued

Biological activity
Insecticidal action of the insecticide-comprising gel formulation according to the invention in vapor-producing systems
Mosquito species: *Culex quinquefasciatus*
Room size: 36 $m^3$
Type of room: 1 window open
Temperature: 23–30° C.
Relative humidity in the room: 35–74%
Heating temperature: 100–110° C.
Active compound content: 39.5% of transfluthrin
Amount of formulation: 1.5 g

| | | Film container No. 1 | | | | Film container No. 2 | | | | Film container No. 3 | | | |
|---|---|---|---|---|---|---|---|---|---|---|---|---|---|
| Operating time/test | Number of mosquitoes | KD-action after minutes or hours | | % dead after | | KD-action after minutes or hours | | % dead after | | KD-action after minutes or hours | | % dead after | |
| after days (hours) | after hours | 50% | 100% | 9 h | 24 h | 50% | 100% | 9 h | 24 h | 50% | 100% | 9 h | 24 h |
| (728 hours) | 1 | — | — | 38 | 58 | | | | | — | — | 20 | 20 |
| | 2 | — | — | 13 | 43 | | | | | — | — | 13 | 25 |
| | 3 | — | — | 20 | 25 | | | | | — | — | 15 | 18 |
| | 4 | — | — | 8 | 40 | | | | | — | — | 8 | 33 |
| | 5 | — | — | 13 | 18 | | | | | — | — | 15 | 10 |
| | 6 | — | — | 3 | 10 | | | | | — | — | 3 | 0 |
| | 7 | — | — | 0 | 10 | | | | | — | — | 18 | 20 |
| | 8 | — | — | 3 | 3 | | | | | — | — | 0 | 8 |

TABLE 6

Biological activity
Insecticidal action of the insecticide-comprising gel formulation according to the invention in vapor-producing systems
Mosquito species: *Aedes aegypti*
Room size: 36 $m^3$
Type of room:
1 window open
Temperature: 23–29° C.
Relative humidity in the room: 25–63%
Heating temperature: 95° C.
Active compound content: 39.5% of transfluthrin
Amount of formulation: 1.5 g

| | | Film container No. 4 | | | | Film container No. 5 | | | |
|---|---|---|---|---|---|---|---|---|---|
| Operating time/test | Number of mosquitoes | KD-action after minutes or hours | | % dead after | | KD-action after minutes or hours | | % dead after | |
| after days (hours) | after hours | 50% | 100% | 9 h | 24 h | 50% | 100% | 9 h | 24 h |
| 0 days | 0 | 1h06' | 1h22' | 100 | 100 | 1h19' | 1h29' | 100 | 100 |
| | 1 | 18' | 25' | 100 | 100 | 21' | 27' | 100 | 100 |
| | 2 | 24' | 31' | 100 | 100 | 23' | 29' | 100 | 100 |
| | 3 | 29' | 38' | 100 | 100 | 21' | 30' | 100 | 100 |
| | 4 | 21' | 36' | 100 | 100 | 18' | 24' | 100 | 100 |
| | 5 | 16' | 23' | 100 | 100 | 16' | 22' | 100 | 100 |
| | 6 | 11' | 17' | 100 | 100 | 9' | 15' | 100 | 100 |
| | 7 | 12' | 19' | 100 | 100 | 10' | 16' | 100 | 100 |
| | 8 | 10' | 14' | 100 | 100 | 9' | 14' | 100 | 100 |
| 1 day | 0 | 42' | 47' | 100 | 100 | 39' | 45' | 100 | 100 |
| (8 hours) | 1 | 21' | 35' | 100 | 100 | 28' | 40' | 100 | 100 |
| | 2 | 21' | 37' | 100 | 100 | 17' | 32' | 100 | 100 |
| | 3 | 19' | 31' | 100 | 100 | 16' | 23' | 100 | 100 |
| | 4 | 17' | 28' | 100 | 100 | 13' | 17' | 100 | 100 |
| | 5 | 13' | 19' | 100 | 100 | 12' | 16' | 100 | 100 |
| | 6 | 15' | 29' | 100 | 100 | 17' | 30' | 100 | 100 |
| | 7 | 21' | 40' | 100 | 100 | 21' | 33' | 100 | 100 |
| | 8 | 16' | 25' | 100 | 100 | 18' | 27' | 100 | 100 |
| 2 days | 0 | 54' | 1h13' | 100 | 100 | 52' | 1h14' | 100 | 100 |
| (16 hours) | 1 | 44' | 58' | 100 | 100 | 40' | 52' | 100 | 100 |
| | 2 | 38' | 49' | 100 | 100 | 32' | 45' | 100 | 100 |
| | 3 | 39' | 54' | 100 | 100 | 38' | 49' | 100 | 100 |
| | 4 | 36' | 45' | 100 | 100 | 29' | 42' | 100 | 100 |
| | 5 | 26' | 38' | 100 | 100 | 26' | 36' | 100 | 100 |
| | 6 | 19' | 28' | 100 | 100 | 20' | 34' | 100 | 100 |
| | 7 | 17' | 26' | 100 | 100 | 18' | 26' | 100 | 100 |

TABLE 6-continued

Biological activity
Insecticidal action of the insecticide-comprising gel formulation according to the invention in vapor-producing systems
Mosquito species: *Aedes aegypti*
Room size: 36 $m^3$
Type of room:
1 window open
Temperature: 23–29° C.
Relative humidity in the room: 25–63%
Heating temperature: 95° C.
Active compound content: 39.5% of transfluthrin
Amount of formulation: 1.5 g

| | | Film container No. 4 | | | | Film container No. 5 | | | |
|---|---|---|---|---|---|---|---|---|---|
| Operating time/test | Number of mosquitoes | KD-action after minutes or hours | | % dead after | | KD-action after minutes or hours | | % dead after | |
| after days (hours) | after hours | 50% | 100% | 9 h | 24 h | 50% | 100% | 9 h | 24 h |
| | 8 | 17' | 24' | 100 | 100 | 24' | 34' | 100 | 100 |
| 7 days | 0 | 32' | 39' | 100 | 100 | 41' | 49' | 100 | 100 |
| (56 hours) | 1 | 12' | 20' | 100 | 100 | 12' | 18' | 100 | 100 |
| | 2 | 17' | 26' | 100 | 100 | 14' | 18' | 100 | 100 |
| | 3 | 12' | 18' | 100 | 100 | 12' | 18' | 100 | 100 |
| | 4 | 11' | 22' | 100 | 100 | 11' | 19' | 100 | 100 |
| | 5 | 13' | 21' | 100 | 100 | 8' | 17' | 100 | 100 |
| | 6 | 14' | 19' | 100 | 100 | 9' | 17' | 100 | 100 |
| | 7 | 12' | 20' | 100 | 100 | 10' | 18' | 100 | 100 |
| | 8 | 10' | 15' | 100 | 100 | 10' | 14' | 100 | 100 |
| 14 days | 0 | 48' | 59' | 100 | 100 | 50' | 53' | 100 | 100 |
| (112 hours) | 1 | 25' | 39' | 100 | 100 | 16' | 25' | 100 | 100 |
| | 2 | 12' | 23' | 100 | 100 | 13' | 22' | 100 | 100 |
| | 3 | 13' | 24' | 100 | 100 | 10' | 14' | 100 | 100 |
| | 4 | 18' | 35' | 100 | 100 | 13' | 17' | 100 | 100 |
| | 5 | 12' | 19' | 100 | 100 | 11' | 15' | 100 | 100 |
| | 6 | 12' | 23' | 100 | 100 | 8' | 12' | 100 | 100 |
| | 7 | 10' | 14' | 100 | 100 | 8' | 12' | 100 | 100 |
| | 8 | 8' | 13' | 100 | 100 | 8' | 13' | 100 | 100 |
| 21 days | 0 | 38' | 55' | 100 | 100 | 30' | 41' | 100 | 100 |
| (168 hours) | 1 | 27' | 39' | 100 | 100 | 22' | 30' | 100 | 100 |
| | 2 | 15' | 20' | 100 | 100 | 15' | 19' | 100 | 100 |
| | 3 | 15' | 21' | 100 | 100 | 16' | 23' | 100 | 100 |
| | 4 | 16' | 22' | 100 | 100 | 15' | 23' | 100 | 100 |
| | 5 | 17' | 24' | 100 | 100 | 15' | 21' | 100 | 100 |
| | 6 | 18' | 25' | 100 | 100 | 14' | 19' | 100 | 100 |
| | 7 | 17' | 27' | 100 | 100 | 15' | 21' | 100 | 100 |
| | 8 | 19' | 28' | 100 | 100 | 13' | 19' | 100 | 100 |
| 28 days | 0 | 29' | 37' | 100 | 100 | 32' | 38' | 100 | 100 |
| (224 hours) | 1 | 21' | 35' | 100 | 100 | 19' | 34' | 100 | 100 |
| | 2 | 19' | 25' | 100 | 100 | 19' | 23' | 100 | 100 |
| | 3 | 18' | 24' | 100 | 100 | 16' | 20' | 100 | 100 |
| | 4 | 22' | 32' | 100 | 100 | 18' | 27' | 100 | 100 |
| | 5 | 21' | 33' | 100 | 100 | 17' | 23' | 100 | 100 |
| | 6 | 20' | 24' | 100 | 100 | 16' | 22' | 100 | 100 |
| | 7 | 19' | 25' | 100 | 100 | 18' | 24' | 100 | 100 |
| | 8 | 18' | 24' | 100 | 100 | 18' | 24' | 100 | 100 |
| 35 days | 0 | 43' | 1h12' | 100 | 100 | 51' | 1h16' | 100 | 100 |
| (280 hours) | 1 | 41' | 51' | 100 | 100 | 34' | 46' | 100 | 100 |
| | 2 | 32' | 40' | 100 | 100 | 29' | 37' | 100 | 100 |
| | 3 | 30' | 42' | 100 | 100 | 25' | 37' | 100 | 100 |
| | 4 | 23' | 34' | 100 | 100 | 23' | 32' | 100 | 100 |
| | 5 | 21' | 31' | 100 | 100 | 24' | 33' | 100 | 100 |
| | 6 | 23' | 30' | 100 | 100 | 24' | 33' | 100 | 100 |
| | 7 | 19' | 27' | 100 | 100 | 18' | 27' | 100 | 100 |
| | 8 | 20' | 29' | 100 | 100 | 20' | 31' | 100 | 100 |
| 42 days | 0 | 51' | 1h22' | 100 | 100 | 51' | 1h06' | 100 | 100 |
| (336 hours) | 1 | 33' | 46' | 100 | 100 | 30' | 38' | 100 | 100 |
| | 2 | 33' | 44' | 100 | 100 | 30' | 37' | 100 | 100 |
| | 3 | 27' | 42' | 100 | 100 | 24' | 31' | 100 | 100 |
| | 4 | 26' | 40' | 100 | 100 | 25' | 33' | 100 | 100 |
| | 5 | 18' | 25' | 100 | 100 | 17' | 23' | 100 | 100 |
| | 6 | 18' | 23' | 100 | 100 | 16' | 20' | 100 | 100 |
| | 7 | 14' | 20' | 100 | 100 | 13' | 18' | 100 | 100 |
| | 8 | 12' | 18' | 100 | 100 | 9' | 17' | 100 | 100 |
| 49 days | 0 | 53' | 1h27' | 100 | 100 | 50' | 1h18' | 100 | 100 |
| (392 hours) | 1 | 39' | 55' | 100 | 100 | 40' | 54' | 100 | 100 |
| | 2 | 39' | 52' | 100 | 100 | 39' | 52' | 100 | 100 |
| | 3 | 33' | 44' | 100 | 100 | 28' | 39' | 100 | 100 |

TABLE 6-continued

Biological activity
Insecticidal action of the insecticide-comprising gel formulation according to the invention in vapor-producing systems
Mosquito species: *Aedes aegypti*
Room size: 36 $m^3$
Type of room:
1 window open
Temperature: 23–29° C.
Relative humidity in the room: 25–63%
Heating temperature: 95° C.
Active compound content: 39.5% of transfluthrin
Amount of formulation: 1.5 g

| | | Film container No. 4 | | | | Film container No. 5 | | | |
|---|---|---|---|---|---|---|---|---|---|
| Operating time/test | Number of mosquitoes | KD-action after minutes or hours | | % dead after | | KD-action after minutes or hours | | % dead after | |
| after days (hours) | after hours | 50% | 100% | 9 h | 24 h | 50% | 100% | 9 h | 24 h |
| | 4 | 21' | 35' | 100 | 100 | 18' | 25' | 100 | 100 |
| | 5 | 19' | 27' | 100 | 100 | 15' | 23' | 100 | 100 |
| | 6 | 16' | 23' | 100 | 100 | 14' | 19' | 100 | 100 |
| | 7 | 13' | 19' | 100 | 100 | 14' | 17' | 100 | 100 |
| | 8 | 14' | 20' | 100 | 100 | 15' | 19' | 100 | 100 |
| 56 days | 0 | 1h02' | 1h31' | 100 | 100 | 56' | 1h17' | 100 | 100 |
| (448 hours) | 1 | 34' | 47' | 100 | 100 | 32' | 45' | 100 | 100 |
| | 2 | 30' | 44' | 100 | 100 | 23' | 30' | 100 | 100 |
| | 3 | 24' | 34' | 100 | 100 | 19' | 26' | 100 | 100 |
| | 4 | 25' | 36' | 100 | 100 | 21' | 29' | 100 | 100 |
| | 5 | 31' | 40' | 100 | 100 | 22' | 32' | 100 | 100 |
| | 6 | 28' | 38' | 100 | 100 | 21' | 29' | 100 | 100 |
| | 7 | 23' | 34' | 100 | 100 | 19' | 26' | 100 | 100 |
| | 8 | 23' | 35' | 100 | 100 | 18' | 27' | 100 | 100 |
| 63 days | 0 | 51' | 1h07' | 100 | 100 | 44' | 59' | 100 | 100 |
| (504 hours) | 1 | 29' | 39' | 100 | 100 | 23' | 32' | 100 | 100 |
| | 2 | 25' | 34' | 100 | 100 | 20' | 26' | 100 | 100 |
| | 3 | 25' | 33' | 100 | 100 | 20' | 28' | 100 | 100 |
| | 4 | 28' | 36' | 100 | 100 | 22' | 30' | 100 | 100 |
| | 5 | 21' | 27' | 100 | 100 | 17' | 25' | 100 | 100 |
| | 6 | 19' | 24' | 100 | 100 | 17' | 22' | 100 | 100 |
| | 7 | 16' | 22' | 100 | 100 | 14' | 18' | 100 | 100 |
| | 8 | 15' | 20' | 100 | 100 | 15' | 19' | 100 | 100 |
| 69 days | 0 | 1h06' | 1h22' | 100 | 100 | 46' | 1h03' | 100 | 100 |
| (552 hours) | 1 | 58' | 1h11' | 100 | 100 | 47' | 57' | 100 | 100 |
| | 2 | 36' | 47' | 100 | 100 | 25' | 32' | 100 | 100 |
| | 3 | 36' | 50' | 100 | 100 | 20' | 28' | 100 | 100 |
| | 4 | 32' | 46' | 100 | 100 | 23' | 29' | 100 | 100 |
| | 5 | 31' | 43' | 100 | 100 | 19' | 25' | 100 | 100 |
| | 6 | 29' | 41' | 100 | 100 | 15' | 20' | 100 | 100 |
| | 7 | 26' | 33' | 100 | 100 | 15' | 22' | 100 | 100 |
| | 8 | 20' | 28' | 100 | 100 | 12' | 17' | 100 | 100 |
| 79 days | 0 | 1h03' | 1h37' | 100 | 100 | 43' | 1h06' | 100 | 100 |
| (832 hours) | 1 | 42' | 1h00' | 100 | 100 | 36' | 43' | 100 | 100 |
| | 2 | 39' | 55' | 100 | 100 | 30' | 36' | 100 | 100 |
| | 3 | 35' | 51' | 100 | 100 | 22' | 29' | 100 | 100 |
| | 4 | 24' | 33' | 100 | 100 | 17' | 21' | 100 | 100 |
| | 5 | 21' | 32' | 100 | 100 | 15' | 19' | 100 | 100 |
| | 6 | 16' | 21' | 100 | 100 | 16' | 20' | 100 | 100 |
| | 7 | 15' | 18' | 100 | 100 | 15' | 19' | 100 | 100 |
| | 8 | 15' | 20' | 100 | 100 | 15' | 18' | 100 | 100 |
| 85 days | 0 | 1h12' | 1h25' | 100 | 100 | 1h01' | 1h15' | 100 | 100 |
| (680 hours) | 1 | 48' | 1h10' | 100 | 100 | 34' | 46' | 100 | 100 |
| | 2 | 37' | 1h04' | 100 | 100 | 29' | 38' | 100 | 100 |
| | 3 | 37' | 56' | 100 | 100 | 28' | 38' | 100 | 100 |
| | 4 | 28' | 44' | 100 | 100 | 25' | 38' | 100 | 100 |
| | 5 | 27' | 40' | 100 | 100 | 19' | 25' | 100 | 100 |
| | 6 | 21' | 30' | 100 | 100 | 17' | 25' | 100 | 100 |
| | 7 | 19' | 25' | 100 | 100 | 16' | 23' | 100 | 100 |
| | 8 | 17' | 21' | 100 | 100 | 15' | 20' | 100 | 100 |

TABLE 7

Biological activity
Insecticidal action of the insecticide-comprising gel formulation according to the invention in vapor-producing systems
Mosquito species: *Culex quinquefasciatus*
Room size: 36 $m^3$
Type of room: 1 window open
Temperature: 23–29° C.
Relative humidity in the room: 25–63%
Heating temperature: 95° C.
Active compound content: 39.5% of transfluthrin
Amount of formulation: 1.5 g

| | | Film container No. 4 | | | | Film container No. 5 | | | |
|---|---|---|---|---|---|---|---|---|---|
| Operating time/test | Number of mosquitoes | KD-action after minutes or hours | | % dead after | | KD-action after minutes or hours | | % dead after | |
| after days (hours) | after hours | 50% | 100% | 9 h | 24 h | 50% | 100% | 9 h | 24 h |
| 0 days | 0 | 8h15' | — | 65 | 53 | — | — | 30 | 23 |
| | 1 | >8h | — | 50 | 55 | — | — | 45 | 55 |
| | 2 | — | — | 45 | 55 | 5h55' | — | 75 | 73 |
| | 3 | — | — | 45 | 55 | — | — | 30 | 40 |
| | 4 | — | — | 13 | 15 | — | — | 40 | 38 |
| | 5 | — | — | 15 | 23 | — | — | 20 | 20 |
| | 6 | — | — | 0 | 3 | — | — | 0 | 8 |
| | 7 | — | — | 0 | 0 | — | — | 0 | 0 |
| | 8 | — | — | 0 | 0 | — | — | 0 | 0 |
| 1 day | 0 | 4h03' | — | 95 | 98 | 5h59' | — | 73 | 85 |
| (8 hours) | 1 | 6h10' | — | 75 | 78 | 4h13' | — | 88 | 93 |
| | 2 | 4h28' | — | 80 | 93 | 3h39' | — | 88 | 100 |
| | 3 | 4h40' | — | 60 | 70 | — | — | 48 | 50 |
| | 4 | — | — | 13 | 10 | — | — | 30 | 38 |
| | 5 | — | — | 13 | 15 | — | — | 8 | 8 |
| | 6 | — | — | 3 | 10 | — | — | 5 | 10 |
| | 7 | — | — | 0 | 0 | — | — | 0 | 0 |
| | 8 | — | — | 0 | 0 | — | — | 0 | 0 |
| 2 days | 0 | — | — | 23 | 25 | — | — | 8 | 8 |
| (16 hours) | 1 | — | — | 5 | 13 | — | — | 10 | 13 |
| | 2 | — | — | 0 | 0 | — | — | 3 | 3 |
| | 3 | — | — | 0 | 0 | — | — | 0 | 0 |
| | 4 | — | — | 0 | 0 | — | — | 0 | 0 |
| | 5 | — | — | 0 | 0 | — | — | 0 | 0 |
| | 6 | — | — | 0 | 0 | — | — | 0 | 0 |
| | 7 | — | — | 0 | 0 | — | — | 0 | 0 |
| | 8 | — | — | 0 | 0 | — | — | 0 | 0 |
| 7 days | 0 | 6h25' | — | 88 | 65 | 6h10' | — | 80 | 50 |
| (56 hours) | 1 | 5h43' | — | 83 | 80 | 6h20' | — | 68 | 35 |
| | 2 | 5h08' | — | 63 | 63 | — | — | 23 | 20 |
| | 3 | 5h10' | — | 50 | 45 | — | — | 43 | 43 |
| | 4 | — | — | 28 | 30 | — | — | 18 | 18 |
| | 5 | — | — | 8 | 5 | — | — | 20 | 18 |
| | 6 | — | — | 15 | 18 | — | — | 5 | 8 |
| | 7 | — | — | 0 | 0 | — | — | 3 | 3 |
| | 8 | — | — | 0 | 0 | — | — | 0 | 0 |
| 14 days | 0 | 5h38' | — | 100 | 100 | 4h40' | 6h50' | 100 | 100 |
| (112 hours) | 1 | 4h15' | — | 100 | 95 | 3h25' | 5h30' | 100 | 100 |
| | 2 | 4h33' | — | 85 | 83 | 2h55' | 4h58' | 100 | 98 |
| | 3 | 4h23' | — | 88 | 90 | 3h45' | — | 95 | 100 |
| | 4 | 3h58' | — | 80 | 75 | 2h55' | — | 98 | 100 |
| | 5 | — | — | 38 | 50 | 2h48' | — | 93 | 95 |
| | 6 | — | — | 5 | 38 | >3h | — | 60 | 85 |
| | 7 | — | — | 5 | 8 | — | — | 5 | 83 |
| | 8 | — | — | 0 | 10 | — | — | 3 | 5 |
| 21 days | 0 | — | — | 3 | 10 | 52' | — | 80 | 88 |
| (168 hours) | 1 | — | — | 10 | 28 | — | — | 35 | 35 |
| | 2 | — | — | 0 | 5 | — | — | 33 | 48 |
| | 3 | — | — | 20 | 18 | — | — | 25 | 35 |
| | 4 | — | — | 8 | 18 | — | — | 3 | 13 |
| | 5 | — | — | 13 | 28 | — | — | 20 | 20 |
| | 6 | — | — | 3 | 20 | — | — | 10 | 8 |
| | 7 | — | — | 0 | 3 | — | — | 8 | 15 |
| | 8 | — | — | 5 | 13 | — | — | 0 | 25 |
| 28 days | 0 | — | — | 45 | 65 | >9h | — | 55 | 50 |
| (224 hours) | 1 | — | — | 20 | 48 | — | — | 15 | 33 |
| | 2 | — | — | 25 | 50 | — | — | 13 | 35 |
| | 3 | — | — | 5 | 35 | — | — | 3 | 28 |
| | 4 | — | — | 0 | 10 | — | — | 8 | 13 |
| | 5 | — | — | 0 | 3 | — | — | 0 | 10 |

TABLE 7-continued

Biological activity
Insecticidal action of the insecticide-comprising gel formulation according to the invention in vapor-producing systems
Mosquito species: *Culex quinquefasciatus*
Room size: 36 $m^3$
Type of room: 1 window open
Temperature: 23–29° C.
Relative humidity in the room: 25–63%
Heating temperature: 95° C.
Active compound content: 39.5% of transfluthrin
Amount of formulation: 1.5 g

| | | Film container No. 4 | | | | Film container No. 5 | | | |
|---|---|---|---|---|---|---|---|---|---|
| Operating time/test | Number of mosquitoes | KD-action after minutes or hours | | % dead after | | KD-action after minutes or hours | | % dead after | |
| after days (hours) | after hours | 50% | 100% | 9 h | 24 h | 50% | 100% | 9 h | 24 h |
| | 6 | — | — | 0 | 0 | — | — | 0 | 0 |
| | 7 | — | — | 0 | 0 | — | — | 0 | 0 |
| | 8 | — | — | 0 | 0 | — | — | 0 | 0 |
| 35 days | 0 | — | — | 43 | 88 | — | — | 40 | 83 |
| (280 hours) | 1 | — | 7h45' | 68 | 100 | — | — | 48 | 88 |
| | 2 | — | — | 25 | 85 | — | — | 23 | 85 |
| | 3 | — | — | 30 | 88 | — | — | 10 | 90 |
| | 4 | — | — | 13 | 70 | — | — | 18 | 83 |
| | 5 | — | — | 20 | 58 | — | — | 13 | 73 |
| | 6 | — | — | 15 | 45 | — | — | 10 | 48 |
| | 7 | — | — | 15 | 30 | — | — | 18 | 33 |
| | 8 | — | — | 3 | 13 | — | — | 5 | 13 |
| 42 days | 0 | — | — | 30 | 40 | 7h40' | — | 73 | 93 |
| (336 hours) | 1 | — | — | 40 | 93 | 6h03' | — | 68 | 95 |
| | 2 | — | — | 23 | 60 | — | — | 33 | 80 |
| | 3 | — | — | 25 | 63 | >6h | — | 50 | 88 |
| | 4 | — | — | 15 | 38 | 3h43' | — | 60 | 68 |
| | 5 | — | — | 18 | 18 | — | — | 35 | 75 |
| | 6 | — | — | 13 | 20 | — | — | 13 | 80 |
| | 7 | — | — | 0 | 3 | — | — | 0 | 13 |
| | 8 | — | — | 3 | 10 | — | — | 0 | 8 |
| 49 days | 0 | — | — | 28 | 95 | — | — | 18 | 80 |
| (392 hours) | 1 | — | — | 10 | 90 | — | — | 35 | 98 |
| | 2 | — | — | 3 | 80 | — | — | 20 | 83 |
| | 3 | — | — | 5 | 75 | — | — | 10 | 85 |
| | 4 | — | — | 8 | 78 | — | — | 8 | 83 |
| | 5 | — | — | 3 | 50 | — | — | 15 | 60 |
| | 6 | — | — | 0 | 43 | — | — | 15 | 20 |
| | 7 | — | — | 3 | 23 | — | — | 3 | 18 |
| | 8 | — | — | 0 | 8 | — | — | 3 | 15 |
| 56 days | 0 | >9h | — | 58 | 60 | 5h38' | — | 88 | 95 |
| (448 hours) | 1 | 6h18' | — | 68 | 93 | 4h30' | — | 83 | 95 |
| | 2 | — | — | 48 | 78 | 5h28' | — | 95 | 88 |
| | 3 | — | — | 25 | 53 | 3h48' | — | 78 | 100 |
| | 4 | — | — | 13 | 35 | >5h | — | 58 | 100 |
| | 5 | — | — | 23 | 35 | — | — | 48 | 90 |
| | 6 | — | — | 8 | 15 | >3h | — | 50 | 80 |
| | 7 | — | — | 5 | 0 | — | — | 18 | 43 |
| | 8 | — | — | 0 | 0 | — | — | 8 | 13 |
| 63 days | 0 | — | — | 35 | 53 | 5h33' | 8h30' | 100 | 100 |
| (504 hours) | 1 | >8h | — | 55 | 55 | 3h55' | — | 90 | 98 |
| | 2 | >7h | — | 55 | 75 | 5h50' | — | 85 | 88 |
| | 3 | >6h | — | 50 | 80 | 3h58' | — | 80 | 88 |
| | 4 | — | — | 40 | 63 | >5h | — | 50 | 88 |
| | 5 | — | — | 13 | 40 | — | — | 43 | 73 |
| | 6 | — | — | 23 | 28 | — | — | 20 | 63 |
| | 7 | — | — | 3 | 5 | — | — | 8 | 10 |
| | 8 | — | — | 3 | 3 | — | — | 5 | 3 |
| 69 days | 0 | — | — | 20 | 15 | 7h08' | — | 65 | 83 |
| (552 hours) | 1 | — | — | 10 | 33 | 6h40' | — | 75 | 93 |
| | 2 | — | — | 15 | 20 | — | — | 48 | 73 |
| | 3 | — | — | 10 | 13 | — | — | 40 | 83 |
| | 4 | — | — | 3 | 3 | — | — | 15 | 80 |
| | 5 | — | — | 10 | 5 | — | — | 5 | 33 |
| | 6 | — | — | 3 | 5 | — | — | 10 | 28 |
| | 7 | — | — | 0 | 0 | — | — | 10 | 18 |
| | 8 | — | — | 0 | 3 | — | — | 5 | 10 |
| 79 days | 0 | — | — | 5 | 8 | >9h | — | 55 | 60 |
| (632 hours) | 1 | — | — | 10 | 13 | — | — | 45 | 55 |
| | 2 | — | — | 8 | 5 | — | — | 18 | 20 |

TABLE 7-continued

Biological activity
Insecticidal action of the insecticide-comprising gel formulation according to the invention in vapor-producing systems
Mosquito species: *Culex quinquefasciatus*
Room size: 36 $m^3$
Type of room: 1 window open
Temperature: 23–29° C.
Relative humidity in the room: 25–63%
Heating temperature: 95° C.
Active compound content: 39.5% of transfluthrin
Amount of formulation: 1.5 g

| Operating time/test | Number of mosquitoes | Film container No. 4 | | | | Film container No. 5 | | | |
|---|---|---|---|---|---|---|---|---|---|
| | | KD-action after minutes or hours | | % dead after | | KD-action after minutes or hours | | % dead after | |
| after days (hours) | after hours | 50% | 100% | 9 h | 24 h | 50% | 100% | 9 h | 24 h |
| | 3 | — | — | 0 | 5 | — | — | 20 | 23 |
| | 4 | — | — | 0 | 0 | — | — | 5 | 10 |
| | 5 | — | — | 0 | 0 | — | — | 5 | 13 |
| | 6 | — | — | 0 | 0 | — | — | 0 | 0 |
| | 7 | — | — | 0 | 0 | — | — | 0 | 0 |
| | 8 | — | — | 0 | 0 | — | — | 0 | 0 |
| 85 days | 0 | — | — | 0 | 13 | — | — | 0 | 15 |
| (680 hours) | 1 | — | — | 0 | 13 | — | — | 0 | 25 |
| | 2 | — | — | 0 | 8 | — | — | 0 | 20 |
| | 3 | — | — | 0 | 10 | — | — | 0 | 15 |
| | 4 | — | — | 0 | 5 | — | — | 0 | 10 |
| | 5 | — | — | 0 | 0 | — | — | 0 | 5 |
| | 6 | — | — | 0 | 0 | — | — | 0 | 8 |
| | 7 | — | — | 0 | 0 | — | — | 0 | 0 |
| | 8 | — | — | 0 | 0 | — | — | 0 | 0 |

We claim:

1. A gel formulation for vapor-producing systems for the controlled and sustained release of an insecticidally active compound, the formulations comprising at least one insecticidally active pyrethroid compound selected from the group consisting of 2,3,5,6-tetrafluorobenzyl(+)-1R-trans-2,2-dimethyl-3-(2,2-dichlorovinyl)-cyclopropane-carboxylate, 2-methyl-3-propargyl-4-oxo-2-cyclopenten-1-yl2,2-dimethyl-3-(2-methylpropenyl)-cyclopropane carboxylate, 3-allyl-2-methylcyclopent-2-en-4-on-1-yl D-cis/trans-chrysanthemate, 1-ethinyl-2-methyl-2-pentenyl 2,2-dimethyl-3-(2-methyl-1-propenyl)-cyclopropane-carboxylate, natural pyrethrum, and mixtures thereof, a silica gel former and at least one vaporization modifier selected from the group consisting of ortho-terphenyl, meta-terphenyl, para-terphenyl and isomeric mixtures of partially hydrogenated terphenyls, wherein the vaporization modifier is present in an amount of 40–80%, the gel former present in an amount of 1–8% add the ratio of active compound/vaporization modifier is between 9 and 0.5.

2. A gel formulation according to claim 1, which comprises between 0.1 and 95% by weight of said insecticidally active compound and 1–90% by weight of said vaporization modifier.

3. A gel formulation according to claim 1, further comprising antioxidants as stabilizers.

4. A gel formulation according to claim 1, in a thermoformed, deep-drawn or cast container made of polymer or metal, said container being open at the top or closed by means of suitable fabric or a film made of polymer or metal, but which is permeable to volatile components for destroying insects.

5. A gel formulation according to claim 1, wherein the ratio of active compound/vaporization modifier is between 9 and 0.5.

6. A gel formulation according to claim 1, further comprising a colorant for visually detecting the end of the biological activity.

7. A gel formulation according to claim 1, wherein said insecticidally active compound is 2,3,5,6-tetrafluorobenzyl (+)-1R-trans-2,2-dimethyl-3-(2,2-dichlorovinyl)-cyclopropane-carboxylate (transfluthrin).

8. A gel formulation according to claim 1, wherein said insecticidally active compound is 2-methyl-3-propargyl-4-oxo-2-cyclopenten-1-yl 2,2-dimethyl-3-(2-methylpropenyl)-cyclopropane carboxylate (prallethrin).

9. A gel formulation according to claim 1, wherein said insecticidally active compound is 3-allyl-2-methylcyclopent-2-en-4-on-1-yl D-cis/trans-chrysanthemate (Pynamin forte®).

10. A gel formulation according to claim 1, wherein said insecticidally active compound is 1-ethinyl-2-methyl-2-pentenyl 2,2-dimethyl-3-(2-methyl-1-propenyl)-cyclopropane-carboxylate.

11. A gel formulation according to claim 1, wherein said insecticidally active compound is natural pyrethrum.

* * * * *